US007422848B2

(12) United States Patent
Bozdayi

(10) Patent No.: US 7,422,848 B2
(45) Date of Patent: Sep. 9, 2008

(54) HEPATITIS-B VIRAL VARIANTS WITH REDUCED SUSCEPTIBILITY TO NUCLEOSIDE ANALOGS AND USES THEREOF

(75) Inventor: Mithat Bozdayi, Ankara (TR)

(73) Assignee: Innogenetics N.V., Ghent (BE)

( * ) Notice: Subject to any disclaimer, the term of this patent is extended or adjusted under 35 U.S.C. 154(b) by 0 days.

(21) Appl. No.: 11/375,585

(22) Filed: Mar. 15, 2006

(65) Prior Publication Data

US 2006/0234212 A1 Oct. 19, 2006

Related U.S. Application Data

(60) Provisional application No. 60/661,484, filed on Mar. 15, 2005.

(30) Foreign Application Priority Data

Mar. 15, 2005 (EP) .................................. 05101997

(51) Int. Cl.
   C12Q 1/70 (2006.01)
   A61K 39/29 (2006.01)
   G01N 31/00 (2006.01)
   G01N 33/00 (2006.01)
   A61K 39/165 (2006.01)

(52) U.S. Cl. .......................... 435/5; 424/227.1; 436/16; 436/89

(58) Field of Classification Search ...................... None
See application file for complete search history.

(56) References Cited

U.S. PATENT DOCUMENTS

| 6,555,311 | B1 | 4/2003 | Locarnini |
| 2003/0124096 | A1 | 7/2003 | Locarnini |
| 2006/0165725 | A1 | 7/2006 | Bozdayi |
| 2006/0234212 | A1 | 10/2006 | Bozdayi |
| 2007/0042356 | A1 | 2/2007 | Schildgen |

FOREIGN PATENT DOCUMENTS

| WO | WO 94/26904 | 11/1994 |
| WO | 97/40193 | 10/1997 |
| WO | WO 98/21317 | 5/1998 |
| WO | WO 00/58477 | 10/2000 |
| WO | WO 00/61758 | 10/2000 |
| WO | WO 03/066841 | 8/2003 |
| WO | WO 03/087351 | 10/2003 |
| WO | WO 2004/031224 | 4/2004 |

OTHER PUBLICATIONS

Werle et al., Evolution of hepatitis B viral load and viral genome sequence during adefovir dipivoxil therapy, 2004, Journal of Viral Hepatitis, vol. 11, No. 1, pp. 74-83.*
European Search Report dated Dec. 12, 2005, issued connection with corresponding EP 05101997.4.
Bartholomew et al, Lancet 1997; 349: 20-22.
Ling et al, Hepatology 1996; 24:711-713.
Perrillo et al, Gastroenterology 2004; 126:81-90.
Stuyver et al, Hepatology 2001; 33:751-757.
Angus et al, "Resistance to Adefovir Dipivoxil Therapy Associated With the Selection of a Novel Mutation in the HBV Polymerase", Gastroenterology 2003; 125:292-297.
Westland et al, "Week 48 Resistance Surveillance in Two Phase 3 Clinical Studies of Adefovir Dipivoxil for Chronic Hepatitis B", Hepatology 2003; 38:96-103.
Delaney et al, "Functional Analysis of rtV173L, an HBV Polymerase Mutation Frequently Observed in Lamivudine-Resistant Chronic Hepatitis B Patients", Hepatology, vol. 36, No. 4, Pt, 2, 2002, 373A.
Peters et al, "Adefovir Dipivoxil Alone or in Combination With Lamivudine in Patients With Lamivudine-Resistant Chronic Hepatitis B", Gastroenterology 2004; 126(1):91-101.
Xiong et al, "Mutations in Hepatitis B DNA Polymerase Associated With Resistance to Lamivudine Do Not Confer Resistance to Adefovir In Vitro", Hepatology 1998; 28:1669-1673.
Yang et al, "Complete Genotypic and Phenotypic Analyses of HBV Mutations Identified in HBeAg-Negative Chronic Hepatitis B Patients Receiving 96 Weeks of Adefovir Dipivoxil (ADV)", Hepatology, vol. 38, No. 4. Suppl. 1, 2003, 705A.
Alexopoulou A et al, J General Virology (1996), vol. 3, pp. 173-181, "Whole genome analysis of hepatitis B virus from four cases of fulminant hepatitis: genetic variability and its potential role in disease pathogenicity" Table 3.
Aye et al, "Hepatitis B Virus Polymerase Mutations During Famciclovir Therapy in Patients Following Liver Transplantation", Hepatology vol. 24, No. 4, Pt.2, Abstract 633, Sep. 1996.
Aye et al, "Hepatitis B Virus polymerase mutations during antiviral therapy in a patient following liver transplantation", Journal of Hepatology, 1997; 26: 1148-1153.
Bartholomeusz et al, "Mutations in the hepatitis B virus polymerase gene that are associated with resistance to famciclovir and lamivudine", 1997, International Antiviral News , vol. 5, No. 8, pp. 123-124.
Bowyer S et al, J General Virology (1997), vol. 78, pp. 1719-1729, "A unique segment of the hepatitis B virus group A genotype identified in isolates from South Africa" Figure 5.
Bozdayi et al "A new mutation pattern (YMDD->YSDD) in the YMDD motif of HBV-DNA polymerase gene in chronic B hepatitis infection resistant to lamivudine" Journal of Hepatology, 2001, 34(1):162-162. Meeting Abstract.
Carman et al, "Vaccine-induced escape mutant . . . ", The Lancet, vol. 336, 1990 (8711) pp. 325-329.
Carman, "The clinical significance of surface antigen variants . . . ", Journal of Viral Hepatitis, 1997. 4 (Suppl. 1) 11-20.
Chenault et al, "Patterns of nucleotide sequence variation among cauliflower mosiac virus isolates", (Biochimie 76:3-8, 1994).

(Continued)

*Primary Examiner*—Bruce Campell
*Assistant Examiner*—Benjamin P Blumel
(74) *Attorney, Agent, or Firm*—Nixon & Vanderhye P.C.

(57) ABSTRACT

The present invention relates generally to the field of Hepatitis B variants exhibiting a reduced sensitivity to nucleoside analogues, both in vivo and in vitro. More in particular, reverse transcriptase mutant rtA181S is provided. Present invention provides assays and methods for detecting such variant, which assays are useful in monitoring anti-viral therapeutic regimes and adjusting patient therapy. A diagnostic kit for detecting the presence of an HBV variant in a biological sample has also been described.

8 Claims, 7 Drawing Sheets

Figure 1:
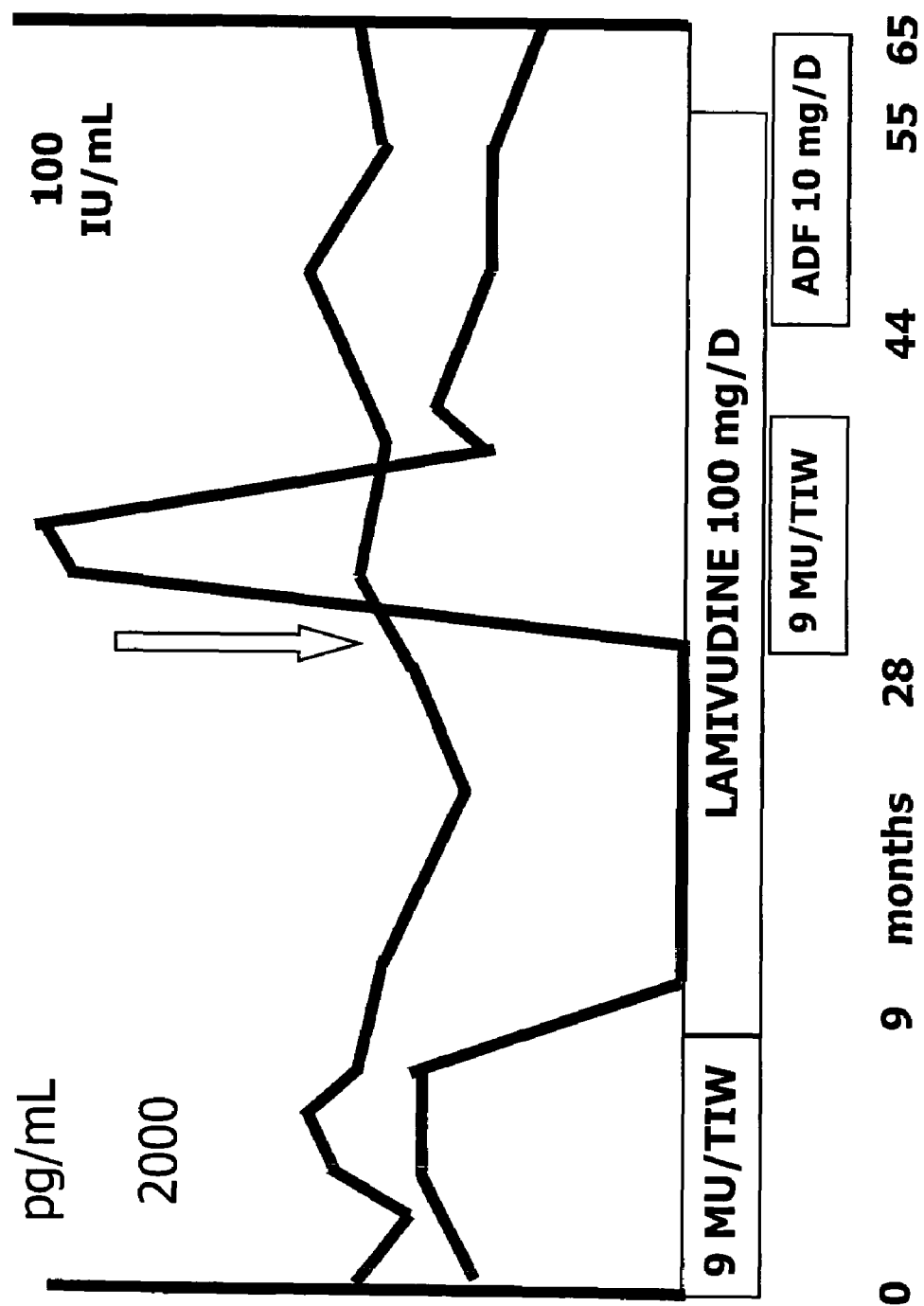

OTHER PUBLICATIONS de Man et al, "The sequential occurrence of viral mutations in a liver transplant recipient re-infected with hepatitis B: hepatitis B immune globulin escape, famciclovir non-respnse, followed by lamivudine resistance resulting in graft loss", Journal of Hepatology, 1998; 29: 669-675.

Delaney et al, "Phenylpropenamide Derivatives AT-61 and AT-130 Inhibit Replication of Wild-Type and Lamivudine-Resistant Strains of Hepatitis B Virus In Vitro", Antimicrobial Agents and Chemotherapy, Sep. 2002, vol. 46, No. 9, pp. 3057-3060.

Delaney et al, "Resistance of hepatitis B virus to antiviral drugs: current aspects and directions for future investigation", Antiviral Chemistry & Chemotherapy 12:1-35 (2001).

Fischer et al, "Generation of Duck Hepatitis B Virus Polymerase Mutants through Site-Directed Mutagenesis Which Demonstrate Resistance to Lamivudine [(-)-β-L-2',3'-Dideoxy-3'-Thiacytidine] In Vitro", Antimicrobial Agents & Chemotherapy 40: 1957-1960, Aug. 1996.

Fujii et al, "Gly$^{145}$ to Arg Substitution in HBs Antigen of . . . ", Biochemical and Biophysical Research Communications, vol. 184, No. 3, May. 15, 1992, pp. 1152-1157.

Gaillard et al, "Kinetic Analysis of Wild-Type and YMDD Mutant Hepatitis B Virus Polymerases and Effects of Deoxyribonucleotide Concentrations on Polymerase Activity", Antimicrobial Agents and Chemotherapy, Apr. 2002, vol. 46, No. 4, pp. 1005-1013.

Gerner et al, "Hepatitis B Virus Core Promoter Mutations in Children with Multiple Anti-HBe/HBeAg Reactivations Result in Enhanced Promoter Activity", Journal of Medical Virology 59:415-423 (1999).

Han et al, "YMDD Motif Mutants in Hepatitis B Virus Polymerase during Lamivudine Therapy", Korean J. Genetics 24(2):219-226 (Jun. 2002).

Ho et al, "A Family Cluster of an Immune Escape Variant of Hepatitis B Virus Infecting a Mother and Her Two Fully Immunized Children", Clinical and Diagnostic Laboratory Immunology, 1995, vol. 2, No. 6, pp. 760-762.

Horikita M et al, J Medical Virology (1994), vol. 44(1), pp. 96-103, "Differences in the entire nucleotide sequence between hepatitis B virus genomes from carriers positive for antibody to hepatitis B e antigen with and without active disease" Table IV.

Ni F et al, Research in Virology (1995), vol. 146(6), pp. 397-407, "A new immune escape mutant of hepatitis B virus with an Asp to Ala substitution in aa144 of the envelope major protein" Figure 3.

Niesters et al, "Identification of a new variant in the YMDD motif of the hepatitis B virus polymerase gene selected during lamivudine therapy", J. Med. Microbiol., vol. 51 (2002), 695-699.

Norder, "Molecular basis of hepatitis B virus serotype variations within the four major subtypes", (Virology 198: 489-503, 1994).

Norder et al, "Molecular basis of hepatitis B virus serotype variations within the four major subtypes", Journal of General Virology 1992, vol. 73, pp. 3141-3145.

Norder H et al, J General Virology (1992), vol. 73(5), pp. 1201-1208, "Comparison of the amino acid sequences of nine different scrotypes of hepatitis B surface antigen and genomic classification of the corresponding hepatitis B strains" Figure 3.

Norder H et al, J General Virology (1993), vol. 74, pp. 1341-1348, "Genetic relatedness of hepatitis B viral strains of diverse geographical origin and natural variations in the primary structure of the surface antigen" Figure 2.

Okamoto F et al, J. General Virology (1988), vol. 69, pp. 2575-2583, "Typing hepatitis B virsu by homology in nucleotide sequence: comparison of surface antigen subtypes" Figure 1.

Ono Y et al, Nucleic Acids Research(1983), vol. 11(6), pp. 1747-1757, "The complete nucleotide of the cloned hepatitis B virus DNA; subtype *adr* and *adw*" Figure 2 and 3.

Pasek M et al, Nature(1979), vol. 282, pp. 575-579, "Hepatitis B virus genes and their expression in *E. coli*" Figure 2.

Poch et al, "Identification of four conserved motifs among the RNA-dependent polymerase encoding elements" EMBO Journal 8: 3867-3874, 1989.

Ren H et al, "Expression of 12 antibody escape mutants of hepatitis B virus surface antigen gene in mammalian cell by using an Epstein-Barr based vector", Chung Hua I Hseuh Tsa Chih 1995 75(7) pages 396-398 (PubMed English Abstract PMID 7553156).

Rivkina M et al, Gene (1988), vol. 64, pp. 285-296, "Nucleotide sequence of integrated hepatitis B virus DNA and human flanking regions in the genome of the PLC/PRF/5 cell line" Figure 5.

Stoll-Becker et al, "Transcription of Hepatitis B Virus in Peripheral Blood Mononuclear Cells from Persistently Infected Patients", Journal of Virology, Jul. 1997, vol. 71, No. 7, pp. 5399-5407.

Tatti et al, "Mutations in the conserved woodchuck hepatitis virus polymerase FLLA and YMDD regions conferring resistance to lamivudine", Antiviral Research 55 (2002) 141-150.

Tipples ("Mutation in HBV RNA-dependent DNA polymerase confers resistance to lamivudine in vivo" Hepatology 24(3): 714-717, Sep. 1996).

Torresi et al, "Restoration of Replication Phenotype of Lamivudine-Resistant Hepatitis B Virus Mutants by Compensatory Changes in the "Fingers" Subdomain of the Viral Polymerase Selected as a Consequence of Mutations in the Overlapping S Gene", Virology 299, 88-99 (2002).

Uchida T et al, J General Virology (1995), vol. 45, pp. 247-252, Complete nucleotide sequences and the characteristics of two hepatitis B virus mutants causing serologically negtive acute or chronic hepatitis B: Page 249.

Uchida, T. et al. GenBank Accession No. D50489, Title: "Direct Submission" Submitted (May 8, 1995) http://www.ncbi.nlm.nih.gov/entrez/viewer.fcgi?db=nuccore&id=807711.

Vaudin M et al, J. General Virology (1988), vol. 69, pp. 1383-1389, "The complete nucleotide sequence of the genome of a hepatitis B virus isolated from a naturally infected chimpanzee" Figure 1.

Wakefield et al, "In Vitro Enzymatic Activity of Human Immunodeficiency Virus Type 1 Reverse Transcriptase Mutants in the Highly Conversed YMDD Amino Acid Motif Correlates with the Infectious Potential of the Proviral Genome", Journal of Virology, Nov. 1992, vol. 66, No. 11, pp. 6806-6812.

Wang GT et al, "Sequencing of hepatitis B virus DNA fragment coding major HBsAg of escape mutant", Chung Hua I Hseuh Tsa Chih Jun. 1994 74(6) pp. 355-357, 391 (PubMed English Abstract PMID 7994645).

Weiss et al, "The HBV-Producing Cell Line HepG2-4A5: A new in vitro system for studying the regulation of HBV replication and for screening anti-hepatitis B virus drugs", Virology 216:214-218, Feb. 1, 1996.

Yamamoto et al, "Naturally Ocurring Escape Mutants of Hepatitis B Virus with . . . ", Journal of Virology, vol. 68, No. 4, Apr. 1994, pp. 2671-2676.

Yan, L. et al, Accession No. Q91F40, submitted (Jun. 2000), title: "Direct Submission", http://www.ncbi.nlm.nih.gov.

Blum, "Variants of Hepatitis B, C and D Viruses: Molecular Biology and Clinical Significance", Digestion (1995); 56:85-95.

Kidd-Ljunggren, "Variability in Hepatitis B Virus DNA: Phylogenetic, Epidemiological and Clinical Implications", Scand J Infect Dig 28:111-116 (1996).

Kan Tan Sui, "Escape Mutants of HBs" (1993), 27(4), pp. 555-562. H. Uetake Ed., Virology, 4$^{th}$ Ed., ver.1, Rikougaku-sha (publ.), Jul. 10, 2002, p. 452 (in Japanese) (Relevance noted in Doc. No. 61).

Aoyama & Partners letter dated Feb. 15, 2007, relating to Japanese Patent Application No. 521944/1998 (4 pages).

Aoyama & Partners letter dated Jan. 25, 2007, relating to Japanese Patent Application No. 521944/1998 (2 pages).

Aoyama & Partners letter dated Jul. 23, 2007, relating to Japanese Patent Application No. 521944/1998 (1 page) with English translation of amended claims (2 pages) and copy of Amendment filed Jul. 19, 2007, in response to Official Action (11 pages).

* cited by examiner

| | 175 L | S | P | F | L | 180 L | A 181 | Q | F | T | S | A | I | C | |
|---|---|---|---|---|---|---|---|---|---|---|---|---|---|---|---|
| HBV D | 654 ctc | agc | ccg | ttt | ctc | ctg | gct | cag | ttt | act | agt | gcc | att | tgt | seq id 9 |
| AA-M28 04/01 | - | - | - | - | - | - | S | - | - | - | - | - | - | - | seq id 1 |
| AA-M31 07/01 | - | - | - | - | - | - | t.. | - | - | - | - | - | - | - | seq id 10 |
| AA-M42 06/02 | - | - | - | - | - | - | S | - | - | - | - | - | - | - | seq id 2 |
| AA-M42 06/02 | - | - | - | - | - | - | t.. | - | - | - | - | - | - | - | seq id 11 |
| AA-M51 03/03 | - | - | - | - | - | - | S | - | - | - | - | - | - | - | seq id 3 |
| AA-M51 03/03 | - | - | - | - | - | - | t.. | - | - | - | - | - | - | - | seq id 11 |
| AA-M57 09/03 | - | - | - | - | - | - | S | - | - | - | - | - | - | - | seq id 3 |
| AA-M57 09/03 | - | - | - | - | - | - | t.. | - | - | - | - | - | - | - | seq id 11 |
| AA-M61 01/04 | - | - | - | - | - | - | S | - | - | - | - | - | - | - | seq id 3 |
| AA-M61 01/04 | - | - | - | - | - | - | t.. | - | - | - | - | - | - | - | seq id 11 |
| AA-M61 01/04 | - | - | - | - | - | - | - | - | - | - | - | - | - | - | seq id 3 |

| | 189 S | V | V | R | R | A | F | P | H | C | L | A | F | S | |
|---|---|---|---|---|---|---|---|---|---|---|---|---|---|---|---|
| HBV D | 696 tca | gtg | gtt | cgt | agg | gct | ttc | ccc | cac | tgt | ttg | gct | ttc | agt | seq id 9 |
| AA-M28 04/01 | - | - | - | - | - | - | - | - | - | - | - | - | - | - | seq id 1 |
| AA-M31 07/01 | - | - | - | - | - | - | - | - | - | - | - | - | - | - | seq id 10 |
| AA-M42 06/02 | - | - | - | - | - | - | - | - | - | - | - | - | - | - | seq id 2 |
| AA-M42 06/02 | - | - | - | - | - | - | - | - | - | - | - | - | - | - | seq id 11 |
| AA-M51 03/03 | - | - | - | - | - | - | - | - | - | - | - | - | - | - | seq id 3 |
| AA-M51 03/03 | - | - | - | - | - | - | - | - | - | - | - | - | - | - | seq id 11 |
| AA-M57 09/03 | - | - | - | - | - | - | - | - | - | - | - | - | - | - | seq id 3 |
| AA-M57 09/03 | - | - | - | - | - | - | - | - | - | - | - | - | - | - | seq id 11 |
| AA-M61 01/04 | - | - | - | - | - | - | - | - | - | - | - | - | - | - | seq id 3 |
| AA-M61 01/04 | - | - | - | - | - | - | - | - | - | - | - | - | - | - | seq id 11 |
| AA-M61 01/04 | - | - | - | - | - | - | - | - | - | - | - | - | - | - | seq id 3 |

Figure 2a

Figure 2b

| | 738 | Y<br>tat | 204<br>M<br>atg | D<br>gat | D<br>gat | V<br>gtg | V<br>gta | L<br>ttg | G<br>ggg | A<br>gcc | K<br>aag | S<br>tct | V<br>gta | Q<br>cag | H<br>cat | |
|---|---|---|---|---|---|---|---|---|---|---|---|---|---|---|---|---|
| HBV D | | tat | atg | gat | gat | gtg | gta | ttg | ggg | gcc | aag | tct | gta | cag | cat | seq id 9 |
| AA-M28 04/01 | | ... | ... | ... | ... | ... | ... | ... | ... | ... | ... | ... | ... | ... | ... | seq id 1 |
| AA-M31 07/01 | | ... | ..I | ... | ... | ... | ... | ... | ... | ... | ... | ... | ... | ... | ... | seq id 10 |
| AA-M31 07/01 | | ... | ..c/t | ... | ... | ... | ... | ... | ... | ... | ... | ... | ... | ... | ... | seq id 2 |
| AA-M42 06/02 | | ... | ..I | ... | ... | ... | ... | ... | ... | ... | ... | ... | ... | ... | ... | seq id 11 |
| AA-M42 06/02 | | ... | ..c/t | ... | ... | ... | ... | ... | ... | ... | ... | ... | ... | ... | ... | seq id 3 |
| AA-M51 03/03 | | ... | ..I | ... | ... | ... | ... | ... | ... | ... | ... | ... | ... | ... | ... | seq id 11 |
| AA-M51 03/03 | | ... | ..c/t | ... | ... | ... | ... | ... | ... | ... | ... | ... | ... | ... | ... | seq id 3 |
| AA-M57 09/03 | | ... | ..I | ... | ... | ... | ... | ... | ... | ... | ... | ... | ... | ... | ... | seq id 11 |
| AA-M57 09/03 | | ... | ..t/c | ... | ... | ... | ... | ... | ... | ... | ... | ... | ... | ... | ... | seq id 3 |
| AA-M61 01/04 | | ... | ..I | ... | ... | ... | ... | ... | ... | ... | ... | ... | ... | ... | ... | seq id 11 |
| AA-M61 01/04 | | ... | ..t/c | ... | ... | ... | ... | ... | ... | ... | ... | ... | ... | ... | ... | seq id 3 |

Figure 3a

|  | 175 L | S | P | F | L | 180 L | A 181 | Q | F | T | S | A | I | C | |
|---|---|---|---|---|---|---|---|---|---|---|---|---|---|---|---|
| HBV D | 654 ctc | agc | ccg | ttt | ctc | ctg | gct | cag | ttt | act | agt | gcc | att | tgt | seq id 9 |
|  | L | S | P | F | L | L | A | Q | F | T | S | A | I | C | seq id 1 |
| AA-M42 clone1 | – | – | – | – | – | M a.. | – | – | – | – | – | – | – | – | seq id 12 |
|  | . | . | . | . | . | . | . | . | . | . | . | . | . | . | seq id 4 |
| AA-M42 clone2 | – | – | – | – | – | – | s.. | – | – | – | – | – | – | – | seq id 11 |
|  | . | . | . | . | . | . | . | . | . | . | . | . | . | . | seq id 5 |
| AA-M42 clone3 | – | – | – | – | – | – | t.. | – | – | – | – | – | – | – | seq id 11 |
|  | . | . | . | . | . | . | s | . | . | . | . | . | . | . | seq id 6 |
| AA-M42 clone4 | – | – | – | – | – | – | t.. | – | – | – | – | – | – | – | seq id 13 |
|  | . | . | . | . | . | . | s | . | . | . | . | . | . | . | seq id 7 |
| AA-M42 clone5 | – | – | – | – | – | M a.. | – | – | – | – | – | – | – | – | seq id 14 |
|  | . | . | . | . | . | . | . | . | . | . | . | . | . | . | seq id 8 |
| AA-M42 clone6 | – | – | – | – | – | – | s.. | – | – | – | – | – | – | – | seq id 11 |
|  | . | . | . | . | . | . | . | . | . | . | . | . | . | . | seq id 6 |
| AA-M42 clone7 | – | – | – | – | – | – | t.. | – | – | – | – | – | – | – | seq id 11 |
|  | . | . | . | . | . | . | s | . | . | . | . | . | . | . | seq id 5 |
|  | . | . | . | . | . | . | t.. | . | . | . | . | . | . | . |  |

| | | | | | | | | | | | | | | | | |
|---|---|---|---|---|---|---|---|---|---|---|---|---|---|---|---|---|
| | 189 | | | | | | | | | | | | | | | |
| | | S | V | V | R | R | A | F | P | H | C | L | A | F | S | seq id 9 |
| HBV D | 696 | tca | gtg | gtt | cgt | agg | gct | ttc | ccc | cac | tgt | ttg | gct | ttc | agt | seq id 1 |
| | | - | - | - | - | - | - | - | - | - | - | - | - | - | - | seq id 12 |
| AA-M42 clone1 | | ... | ... | ... | ... | ... | ... | ... | ... | ... | ... | ... | ... | ... | ... | seq id 4 |
| | | - | - | - | - | - | - | - | - | - | - | - | - | - | - | seq id 11 |
| AA-M42 clone2 | | ... | ... | ... | ... | ... | ... | ... | ... | ... | ... | ... | ... | ... | ... | seq id 5 |
| | | - | - | - | - | - | - | - | - | - | - | - | - | - | - | seq id 11 |
| AA-M42 clone3 | | ... | ... | ... | ... | ... | ... | ... | ... | ... | ... | ... | ... | ... | ... | seq id 6 |
| | | - | - | - | - | - | - | - | - | - | - | - | - | - | - | seq id 13 |
| AA-M42 clone4 | | ... | ... | ... | ... | ... | ... | ... | ... | ... | ... | ... | ... | ... | ... | seq id 7 |
| | | - | - | - | - | - | - | - | - | - | - | - | - | - | - | seq id 14 |
| AA-M42 clone5 | | ... | ... | ... | ... | ... | ... | ... | ... | ... | ... | ... | ... | ... | ... | seq id 8 |
| | | - | - | - | - | - | - | - | - | - | - | - | - | - | - | seq id 11 |
| AA-M42 clone6 | | ... | ... | ... | ... | ... | ... | ... | ... | ... | ... | ... | ... | ... | ... | seq id 6 |
| | | - | - | - | - | - | - | - | - | - | - | - | - | - | - | seq id 11 |
| AA-M42 clone7 | | ... | ... | ... | ... | ... | ... | ... | ... | ... | ... | ... | ... | ... | ... | seq id 5 |

Figure 3b

Figure 3c

| | | 204 | | | | | | | | | | | | | | |
|---|---|---|---|---|---|---|---|---|---|---|---|---|---|---|---|---|
| | Y | M | D | D | V | V | L | G | A | K | S | V | Q | H | | |
| HBV D 738 | tat | atg | gat | gat | gtg | gta | ttg | ggg | gcc | aag | tct | gta | cag | cat | | seq id 9 |
| AA-M42 clone1 | – | .gc<br>S | – | – | – | – | – | – | – | – | – | – | – | – | | seq id 1 |
| AA-M42 clone2 | : | ..t<br>I | : | : | : | : | : | : | : | : | : | : | : | : | | seq id 12 |
| AA-M42 clone3 | – | ..t<br>I | – | – | – | – | – | – | – | – | – | – | – | – | | seq id 4 |
| AA-M42 clone4 | : | ..c<br>I | ..g<br>G | : | : | : | : | : | : | : | : | : | : | : | | seq id 11 |
| AA-M42 clone5 | – | ..c<br>I | ..g | – | – | – | – | ..c<br>R | – | – | – | – | – | – | | seq id 5 |
| AA-M42 clone6 | : | ..c<br>S | : | : | : | : | : | : | : | : | : | : | : | : | | seq id 11 |
| AA-M42 clone7 | – | .gc<br>I | – | – | – | – | – | – | – | – | – | – | – | – | | seq id 6 |
| | : | ..c<br>I | : | : | : | : | : | : | : | : | : | : | : | : | | seq id 13 |
| | – | ..t<br>I | – | – | – | – | – | – | – | – | – | – | – | – | | seq id 7 |
| | : | : | : | : | : | : | : | : | : | : | : | : | : | : | | seq id 14 |
| | – | – | – | – | – | – | – | – | – | – | – | – | – | – | | seq id 8 |
| | : | : | : | : | : | : | : | : | : | : | : | : | : | : | | seq id 11 |
| | – | – | – | – | – | – | – | – | – | – | – | – | – | – | | seq id 6 |
| | : | : | : | : | : | : | : | : | : | : | : | : | : | : | | seq id 11 |
| | ..t | – | – | – | – | – | – | – | – | – | – | – | – | | | seq id 5 |

SEQUENCE LISTING

```
<160> NUMBER OF SEQ ID NOS: 33

<210> SEQ ID NO 1
<211> LENGTH: 126
<212> TYPE: DNA
<213> ORGANISM: Hepatitis B Virus

<400> SEQUENCE: 1
ctcagcccgt ttctcctggc tcagtttact agtgccattt gttcagtggt tcgtagggct      60
ttcccccact gtttggcttt cagttatatg gatgatgtgg tattgggggc caagtctgta    120
cagcat                                                                126

<210> SEQ ID NO 2
<211> LENGTH: 126
<212> TYPE: DNA
<213> ORGANISM: Hepatitis B Virus

<400> SEQUENCE: 2
ctcagcccgt ttctcctgtc tcagtttact agtgccattt gttcagtggt tcgtagggct      60
ttcccccact gtttggcttt cagttatatg gatgatgtgg tattgggggc caagtctgta    120
cagcat                                                                126

<210> SEQ ID NO 3
<211> LENGTH: 126
<212> TYPE: DNA
<213> ORGANISM: Hepatitis B Virus

<400> SEQUENCE: 3
ctcagcccgt ttctcctgtc tcagtttact agtgccattt gttcagtggt tcgtagggct      60
ttcccccact gtttggcttt cagttataty gatgatgtgg tattgggggc caagtctgta    120
cagcat                                                                126

<210> SEQ ID NO 4
<211> LENGTH: 126
<212> TYPE: DNA
<213> ORGANISM: Hepatitis B Virus

<400> SEQUENCE: 4
ctcagcccgt ttctcatggc tcagtttact agtgccattt gttcagtggt tcgtagggct      60
ttcccccact gtttggcttt cagttatagc gatgatgtgg tattgggggc caagtctgta    120
cagcat                                                                126
```

<210> SEQ ID NO 5
<211> LENGTH: 126
<212> TYPE: DNA
<213> ORGANISM: Hepatitis B Virus

<400> SEQUENCE: 5

```
ctcagcccgt ttctcctgtc tcagtttact agtgccattt gttcagtggt tcgtagggct    60
ttcccccact gtttggcttt cagttatatt gatgatgtgg tattgggggc caagtctgta   120
cagcat                                                              126
```

<210> SEQ ID NO 6
<211> LENGTH: 126
<212> TYPE: DNA
<213> ORGANISM: Hepatitis B Virus

<400> SEQUENCE: 6

```
ctcagcccgt ttctcctgtc tcagtttact agtgccattt gttcagtggt tcgtagggct    60
ttcccccact gtttggcttt cagttatatc gatgatgtgg tattgggggc caagtctgta   120
cagcat                                                              126
```

<210> SEQ ID NO 7
<211> LENGTH: 126
<212> TYPE: DNA
<213> ORGANISM: Hepatitis B Virus

<400> SEQUENCE: 7

```
ctcagcccgt ttctcctgtc tcagtttact agtgccattt gttcagtggt tcgtagggct    60
ttcccccact gtttggcttt cagttatatc ggtgatgtgg tattgggggc caagtctgta   120
cagcat                                                              126
```

<210> SEQ ID NO 8
<211> LENGTH: 126
<212> TYPE: DNA
<213> ORGANISM: Hepatitis B Virus

<400> SEQUENCE: 8

```
ctcagcccgt ttctcatggc tcagtttact agtgccattt gttcagtggt tcgtagggct    60
ttcccccact gtttggcttt cagttatagc gatgatgtgg tattgcgggc caagtctgta   120
cagcat                                                              126
```

<210> SEQ ID NO 9
<211> LENGTH: 42
<212> TYPE: PRT
<213> ORGANISM: Hepatitis B Virus

<400> SEQUENCE: 9

```
Leu Ser Pro Phe Leu Leu Ala Gln Phe Thr Ser Ala Ile Cys Ser Val
1               5                  10                  15

Val Arg Arg Ala Phe Pro His Cys Leu Ala Phe Ser Tyr Met Asp Asp
            20                  25                  30

Val Val Leu Gly Ala Lys Ser Val Gln His
        35                  40
```

<210> SEQ ID NO 10
<211> LENGTH: 42
<212> TYPE: PRT
<213> ORGANISM: Hepatitis B Virus

```
<400> SEQUENCE: 10

Leu Ser Pro Phe Leu Leu Ser Gln Phe Thr Ser Ala Ile Cys Ser Val
1               5                   10                  15

Val Arg Arg Ala Phe Pro His Cys Leu Ala Phe Ser Tyr Met Asp Asp
                20                  25                  30

Val Val Leu Gly Ala Lys Ser Val Gln His
            35                  40

<210> SEQ ID NO 11
<211> LENGTH: 42
<212> TYPE: PRT
<213> ORGANISM: Hepatitis B Virus

<400> SEQUENCE: 11

Leu Ser Pro Phe Leu Leu Ser Gln Phe Thr Ser Ala Ile Cys Ser Val
1               5                   10                  15

Val Arg Arg Ala Phe Pro His Cys Leu Ala Phe Ser Tyr Ile Asp Asp
                20                  25                  30

Val Val Leu Gly Ala Lys Ser Val Gln His
            35                  40

<210> SEQ ID NO 12
<211> LENGTH: 42
<212> TYPE: PRT
<213> ORGANISM: Hepatitis B Virus

<400> SEQUENCE: 12

Leu Ser Pro Phe Leu Met Ala Gln Phe Thr Ser Ala Ile Cys Ser Val
1               5                   10                  15

Val Arg Arg Ala Phe Pro His Cys Leu Ala Phe Ser Tyr Ser Asp Asp
                20                  25                  30

Val Val Leu Gly Ala Lys Ser Val Gln His
            35                  40

<210> SEQ ID NO 13
<211> LENGTH: 42
<212> TYPE: PRT
<213> ORGANISM: Hepatitis B Virus

<400> SEQUENCE: 13

Leu Ser Pro Phe Leu Leu Ser Gln Phe Thr Ser Ala Ile Cys Ser Val
1               5                   10                  15

Val Arg Arg Ala Phe Pro His Cys Leu Ala Phe Ser Tyr Ile Gly Asp
                20                  25                  30

Val Val Leu Gly Ala Lys Ser Val Gln His
            35                  40

<210> SEQ ID NO 14
<211> LENGTH: 42
<212> TYPE: PRT
<213> ORGANISM: Hepatitis B Virus

<400> SEQUENCE: 14

Leu Ser Pro Phe Leu Met Ala Gln Phe Thr Ser Ala Ile Cys Ser Val
1               5                   10                  15

Val Arg Arg Ala Phe Pro His Cys Leu Ala Phe Ser Tyr Ser Asp Asp
                20                  25                  30

Val Val Leu Arg Ala Lys Ser Val Gln His
            35                  40
```

<210> SEQ ID NO 15
<211> LENGTH: 12
<212> TYPE: PRT
<213> ORGANISM: Artificial Sequence
<220> FEATURE:
<223> OTHER INFORMATION: Tagu100 epitope

<400> SEQUENCE: 15

Glu Glu Thr Ala Arg Phe Gln Pro Gly Tyr Arg Ser
1               5                   10

<210> SEQ ID NO 16
<211> LENGTH: 10
<212> TYPE: PRT
<213> ORGANISM: Artificial Sequence
<220> FEATURE:
<223> OTHER INFORMATION: c-myc epitope

<400> SEQUENCE: 16

Glu Gln Lys Leu Ile Ser Glu Glu Asp Leu
1               5                   10

<210> SEQ ID NO 17
<211> LENGTH: 7
<212> TYPE: PRT
<213> ORGANISM: Artificial Sequence
<220> FEATURE:
<223> OTHER INFORMATION: FLAG-epitope

<400> SEQUENCE: 17

Asp Tyr Lys Asp Asp Asp Lys
1               5

<210> SEQ ID NO 18
<211> LENGTH: 9
<212> TYPE: PRT
<213> ORGANISM: Artificial Sequence
<220> FEATURE:
<223> OTHER INFORMATION: HA epitope

<400> SEQUENCE: 18

Tyr Pro Tyr Asp Val Pro Asp Tyr Ala
1               5

<210> SEQ ID NO 19
<211> LENGTH: 12
<212> TYPE: PRT
<213> ORGANISM: Artificial Sequence
<220> FEATURE:
<223> OTHER INFORMATION: protein C epitope

<400> SEQUENCE: 19

Glu Asp Gln Val Asp Pro Arg Leu Ile Asp Gly Lys
1               5                   10

<210> SEQ ID NO 20
<211> LENGTH: 11
<212> TYPE: PRT
<213> ORGANISM: Artificial Sequence
<220> FEATURE:
<223> OTHER INFORMATION: VSV epitope

<400> SEQUENCE: 20

Tyr Thr Asp Ile Glu Met Asn Arg Leu Gly Lys
1               5                   10

```
<210> SEQ ID NO 21
<211> LENGTH: 30
<212> TYPE: DNA
<213> ORGANISM: Hepatitis B Virus

<400> SEQUENCE: 21
cacctgcagc ctcatttgt gggtcaccat                                        30

<210> SEQ ID NO 22
<211> LENGTH: 35
<212> TYPE: DNA
<213> ORGANISM: Hepatitis B Virus

<400> SEQUENCE: 22
cataagcttc acaattcgtt gacatacttt ccaat                                 35

<210> SEQ ID NO 23
<211> LENGTH: 31
<212> TYPE: DNA
<213> ORGANISM: Hepatitis B Virus

<400> SEQUENCE: 23
gtgctgcagt ttgtgggtca ccatattctt g                                     31

<210> SEQ ID NO 24
<211> LENGTH: 32
<212> TYPE: DNA
<213> ORGANISM: Hepatitis B Virus

<400> SEQUENCE: 24
gacaagcttt tgacatactt tccaatcaat ag                                    32

<210> SEQ ID NO 25
<211> LENGTH: 41
<212> TYPE: DNA
<213> ORGANISM: Hepatitis B Virus

<400> SEQUENCE: 25
ccggaaagct tgagctcttc tttttcacct ctgcctaatc a                          41

<210> SEQ ID NO 26
<211> LENGTH: 40
<212> TYPE: DNA
<213> ORGANISM: Hepatitis B Virus

<400> SEQUENCE: 26
ccggaaagct tgagctcttc aaaaagttgc atggtgctgg                            40

<210> SEQ ID NO 27
<211> LENGTH: 24
<212> TYPE: DNA
<213> ORGANISM: Hepatitis B Virus

<400> SEQUENCE: 27
tttactagtg ccatttgttc agtg                                             24

<210> SEQ ID NO 28
<211> LENGTH: 25
<212> TYPE: DNA
<213> ORGANISM: Hepatitis B Virus

<400> SEQUENCE: 28
gctccagttc aggaacagta aaccc                                            25
```

```
<210> SEQ ID NO 29
<211> LENGTH: 31
<212> TYPE: DNA
<213> ORGANISM: Hepatitis B Virus

<400> SEQUENCE: 29
cacctgcagc ctcattttgt gggtcaccat a                              31

<210> SEQ ID NO 30
<211> LENGTH: 24
<212> TYPE: DNA
<213> ORGANISM: Hepatitis B Virus

<400> SEQUENCE: 30
ggcaggtccc ctagaagaag aact                                      24

<210> SEQ ID NO 31
<211> LENGTH: 25
<212> TYPE: DNA
<213> ORGANISM: Hepatitis B Virus

<400> SEQUENCE: 31
attgagatct tctgcgacgc ggcga                                     25

<210> SEQ ID NO 32
<211> LENGTH: 24
<212> TYPE: DNA
<213> ORGANISM: Hepatitis B Virus

<400> SEQUENCE: 32
gaccttgagg catatttcaa agac                                      24

<210> SEQ ID NO 33
<211> LENGTH: 23
<212> TYPE: DNA
<213> ORGANISM: Hepatitis B Virus

<400> SEQUENCE: 33
ctgagtgctg tatggtgagg tga                                       23
```

HEPATITIS-B VIRAL VARIANTS WITH REDUCED SUSCEPTIBILITY TO NUCLEOSIDE ANALOGS AND USES THEREOF

This application claims benefit of EP 05101997.4, filed 15 Mar. 2005, and U.S. Provisional Application No. 60/661,484 filed 15 Mar. 2005, the entire contents of each of which are hereby incorporated by reference.

The present invention relates to the field of Hepatitis B virus (HBV, also indicated with HBV virus) variants exhibiting a reduced sensitivity to particular agents. More particularly, the present invention relates to the field of diagnosing the susceptibility of an HBV sample to antiviral drugs used to treat HBV infection and to a method and/or assay for the rapid and reliable detection of drug-induced mutations in the HBV genes allowing the simultaneous characterization of a range of codons involved in drug resistance.

HBV is a small enveloped DNA virus of approximately 3200 bp length belonging to the family of the hepadnaviruses. The virus replicates via an RNA intermediate and utilises reverse transcription in its replication strategy (Summers, 1982). The HBV genome is of a complex nature having a partially double stranded DNA stricture with overlapping open reading frame (ORFs) being (i) the preC/C ORF encoding the secreted e antigen (HBeAg) and nucleocapsid core protein (HBcAg), respectively; (ii) the P ORF encoding the viral polymerase/reverse transcriptase; (iii) the preS1/preS2/S ORF encoding the viral envelope proteins, large, middle and small s antigen (HBsAg), respectively; and (iv) the X ORF encoding a transcriptional trans-activator protein encoding surface, core, polymerase and X genes.

Hepatitis B viruses exhibit a large genetic variability in their genomes, with currently seven HBV genotypes (A to G) being recognized (Stuyver et al., 2001; Stuyver et al., 2000). The virus, which is spread through contact with infected blood, can cause debilitating disease conditions and can lead to acute liver failure. Although most adults can fight off an infection without treatment, hepatitis B infection may develop into a chronic form. Actually, about 400 million people world-wide are chronically infected with HBV and approximately 15 to 40% of chronic HBV carriers are expected to progress to cirrhosis and end-stage liver disease. Without treatment the prognosis for these patients is poor, consequently the development of effective antiviral therapy for HBV remains an important goal. The principle objective of therapy is to control the replication of HBV and induce the remission of hepatic disease in order to stop progression to cirrhosis and hepatic cancer. Treatment is indicated for patients with active inflammation, elevated alanine aminotransferase (ALT) levels due to the destruction of liver cells, and levels of HBV DNA (viral replication levels) higher than 100.000 copies/ml.

Current drugs approved for the treatment of chronic hepatitis B are the alfa-interferons, and nucleoside analogues or combinations of the drugs. A nucleoside analogue is a chemically engineered nucleotide that acts as a substitute building block in the viral replication process, inhibiting the replication of HBV.

Interferon (IFN) therapy has been shown to be partially effective only in a small group of carriers (Lok, 1994) and it is also limited due to severe side effects. This relative failure of IFN-$\alpha$ for the treatment of chronic HBV infection has prompted the search for further therapeutic agents and regimes. In particular, a number of nucleoside analogues has been shown to inhibit hepadnaviral replication via inhibition of the hepadnaviral DNA polymerase/reverse transcriptase. Some of these compounds have already been withdrawn from clinical use due to toxicity (lobucavir) or lack of efficacy (famciclovir) (De Clercq, 1999; Schinazi, 1997; Luscombe et al., 1996). At this moment, the most successful nucleoside analogue for treatment of chronic hepatitis B is without doubt the medically approved (−) enantiomer of 3'-thiacytidine (3TC or lamivudine (LAM)), (Jarvis et al., 1999). The drug has a potent antiviral activity against the virus, is well tolerated and has few adverse effects. However, long term therapy with lamivudine frequently is associated with the emergence of viral resistance. One of the common mutations that confer lamivudine resistance and reduce the in vitro replication efficiency of the virus is a methionine-to-isoleucine or methionine-to-valine substitution at codon 204 of the HBV RNA-dependent DNA (Ling R. et al., 1996; Bartholomew M. et al., 1997; Tipples G. A. et al., 1996). Besides the alteration of this Met-to-Val or to-Ile amino acid substitution (rtM204V/I) at the conserved YMDD motif, mutated genotypic patterns at other sites of the reverse trancriptase gene have been associated to lamivudine resistance. In particular, the leucine-to-methionine mutation at codon 180 (rtL180M) in the B-domain of the polymerase was reported to partially restore replication fitness as well as to augment drug resistance in vitro. In HBV/HIV co-infected patients the development of lamivudine resistance is more frequent than in HBV mono-infected patients, making a therapy alternative to lamivudine application indispensable (Benhamou et al., 2001; Benhamou et al, 2003; Benhamou et al, 2004; Dore G. J. et al, 2004).

Another nucleoside analogue applicable for the treatment of chronic hepatitis B is adefovir dipivoxil, the pro-drug of adefovir (ADF). Studies in vitro and in vivo have demonstrated that this drug is able to inhibit wild-type HBV strains as well as those showing lamivudine resistances. Therefore, ADF may serve as an alternative therapy for treatment of chronic HBV infection in cases where lamivudine resistance has occurred. Hitherto, ADF passed successfully clinical phase III studies (Westland C E et al, 2003.). Two mutations mediating resistance to ADF have already been described. These mutations are located at codon 181 (B-domain) and at codon 236 (D-domain) of the reverse transcriptase gene and result in an amino acid substitution Ala to Val (rtA181V) and Asn to Thr (rtN236T), respectively (Angus P. et al., 2003; Yang H. et al., 2003; WO 2003/087352; WO 2004/031224). The frequency of the mutation rtA181V is about 2.5% with a hitherto unknown clinical relevance, whereas 1.7-2.5% of the adefovir treated patients reveals the resistance mutation rtN236T.

Recently published studies by Perrillo et al. (2004) as well as by Peters et al (2004) demonstrate that approximately 85% to 92% of patients with lamivudine resistance will have a decrease in their HBV DNA level by greater than or equal to two logs while receiving ADF. This implies that 8-15% of patients does not achieve a significant reduction in HBV DNA levels when ADF is added to the therapy. Therefore, there is a precedent for a subgroup of patients with lamivudine resistant HBV that will not achieve a virologic response with ADF therapy. The reason for the non-responsiveness to ADF remains unclear.

Therefore, although lamivudine and adefovir have strong antiviral effects, development of mutants causing drug resistance presents an important problem in the treatment of chronic HBV infections. Moreover, existence of HBV mutation patterns with a cross resistance profile poses a major concern due to possibility of failure of combination therapies. Although studies testing for cross resistance of different antiviral drugs on HBV mutants have been reported (Delaney et al., (2001), Xiong et al., (2001)) no mutation pattern that is responsible for in vivo and in vitro resistance to both adefovir and lamivudine has been documented so far.

From the previous, it seems there is a need to monitor the emergence or presence of HBV variants exhibiting a reduced sensitivity to particular agents, in order to screen for and/or develop and/or design other agents having properties suitable for making them useful in new therapeutic regimes. In accordance with the present invention, the inventors have identified variants of HBV with mutations in the HBV DNA polymerase gene which reduce the sensitivity of HBV to nucleoside analogues.

SUMMARY OF THE INVENTION

The present invention aims to solve the problem of inadequate monitoring of the emergence or presence of HBV variants exhibiting a reduced sensitivity to nucleoside analogues.

The present invention relates to isolated HBV variants that comprise at least one nucleotide mutation in the DNA polymerase gene, wherein said nucleotide mutations result in at least one amino acid substitution in the HBV polymerase and wherein said variant exhibits a decreased sensitivity to the nucleoside analogue ADF and/or LAM and/or their combination.

The present invention further relates to isolated polynucleic acids from these HBV variants, which isolated polynucleic acids comprise a nucleotide mutation that results in at least one amino acid substitution and/or deletion in the polymerase gene and which nucleotide mutation leads to a reduced sensitivity to the nucleotide analogue ADF and/or LAM and/or a their combination; and to a fragment of said HBV polynucleic acid comprising said nucleotide mutation.

The present invention further relates to expression products from these isolated polynucleic acids and to a fragment thereof.

Further aspects of the invention relate to compositions that comprise HBV variants or polynucleic acid or expression products of the present invention, which preferably find their application in the monitoring and/or identification of HBV variants.

Another aspect of the invention relates to the use of the isolated HBV variants and/or their polynucleic acids and/or expression products and/or compositions as described above in clinical decision making. In particular, HBV variants or polynucleic acids or expression products or compositions of the present invention are used in a process for the selection of at least one non-cross resistant anti-HBV drug. In particular, HBV variants or polynucleic acids or expression products or compositions are used in a process for the detection of an HBV variant polynucleic acid.

The present invention further relates to a process for the treatment of HBV infection comprising administering a nucleoside analogue to a subject infected with HBV, determining whether the subject is infected with an HBV variant as described, and if so, administering to the subject at least one non-cross resistant anti-HBV drug.

Further included in the invention are methods aimed to detect the presence of the HBV variants according to the invention in a biological sample. Said method comprises the step of detecting therein the presence of an HBV polynucleic acid or fragment thereof.

Finally, the present invention relates to a diagnostic kit detecting the presence of an HBV variant in a biological sample and/or for detecting resistance to an antiviral drug of an HBV present in a biological sample. Furthermore, a method has been provided for screening for drugs active against an HBV comprising a polynucleic acid as indicated above.

Furthermore an oligonucleotide capable of discriminating, in an HBV polynucleic acid or a fragment thereof, a new codon 181 encoding a serine different from known codons 181 encoding an alanine or a valine, has been provided.

FIGURE LEGENDS

FIG. 1. Schematic presentation of patient history. The X-axis represents the time line. Underneath the X-axis the successive treatments of HBV-infected patient AA are indicated in months (MU/TIW represents million units of interferon three times a week). On the left Y-axis, the viral DNA load (in pg HBV DNA/mL serum as determined using the liquid hybridization assay of Digene, US) is given. The HBV DNA levels in serum samples of patient AA are indicated by the black solid line. On the right Y-axis, the ALT-levels (alanine amino-transferase; in 100 IU/mL, 100 International Units/mL) are given. The vertical arrow at the top of the figure indicates the ALT-flare coinciding with the onset of viral breakthrough.

FIG. 2 (2a and 2b): Alignment of HBV DNA polymerase sequences at different time intervals from the start of antiviral treatment. Aligned are fragments of the HBV D DNA polymerase/reverse transcriptase nucleotide sequence, indicated by SEQ ID NO 1 and corresponding amino acid sequence, indicated by SEQ ID NO 9 derived from the Genebank accession NO X02496, and six HBV DNA polymerase/reverse transcriptase nucleotide sequences and corresponding amino acid sequences obtained from patient AA at different time intervals from the start of antiviral treatment. These six nucleotide sequences are indicated by SEQ ID's 2 and 3, the corresponding amino acid sequences by SEQ ID's 10 and 11, respectively. The serum withdrawal dates are indicated by XX/YY, wherein XX indicates the month and YY indicates the year of withdrawal. The period from the start of the antiviral treatment is indicated by MZZ, in months.

FIG. 3 (3a, 3b and 3c): Alignment of HBV DNA polymerase sequences. Aligned are fragments of the HBV DNA polymerase/reverse transcriptase as described in FIG. 2 and of seven HBV DNA polymerase/reverse transcriptase nucleotide sequences and corresponding amino acid sequences obtained from patient AA at month 42. The serum withdrawal date is February 2002. These seven nucleotide sequences are indicated by SEQ ID's 4 to 8, the corresponding amino acid sequences by SEQ ID's 12 to 14.

Figure 4:
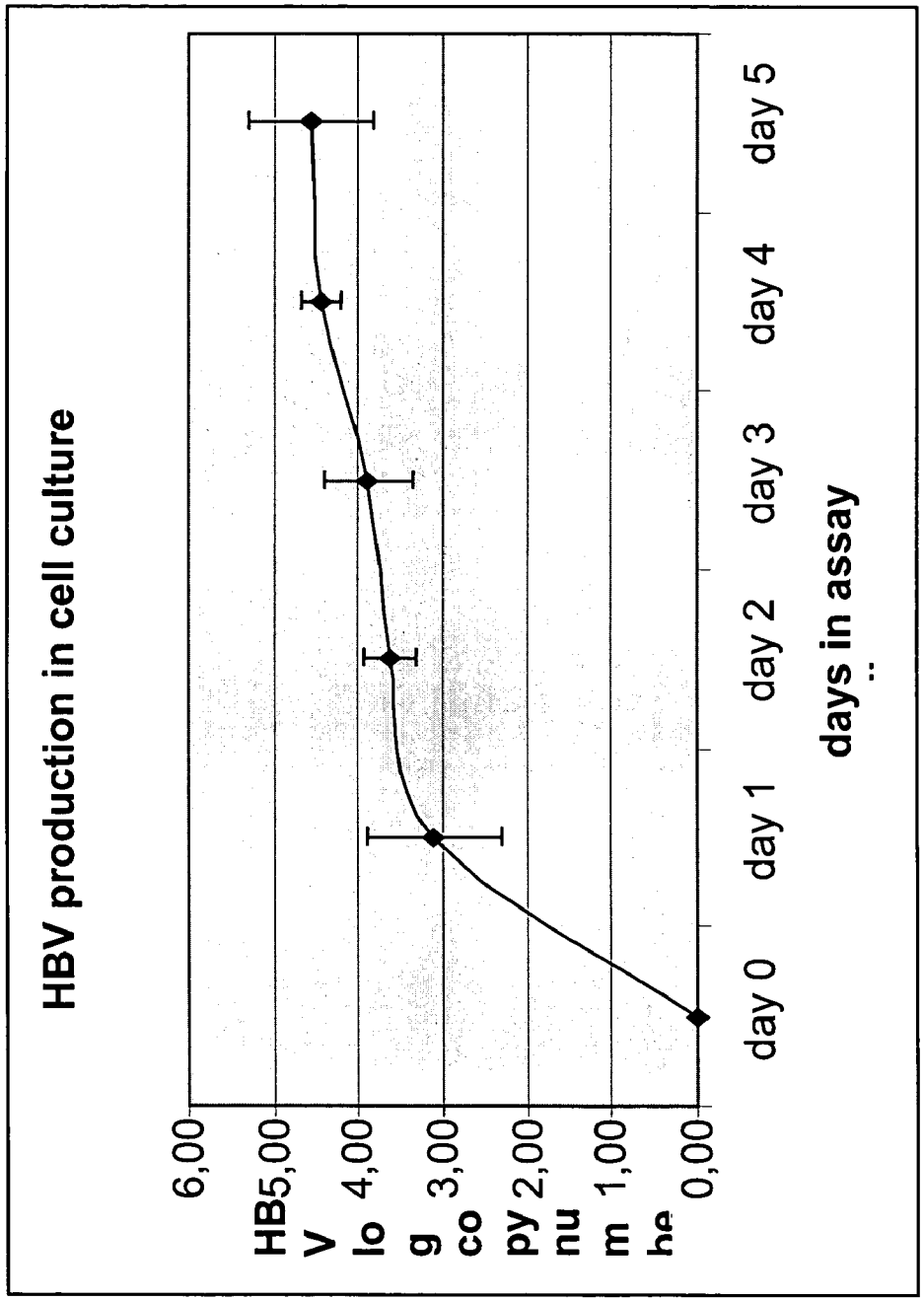

FIG. 4: HBV production in cell culture supernatant of transiently transfected Huh7 cell line. The Log copy number of HBV production on the Y-axis is graphed according to on the X-axis the days in assay medium after transfection with full-length HBV genome within the clone harbouring the A181S+M204I mutation pattern. Day 0 refers to the day prior to transfection of the Huh7 cell line.

DETAILED DESCRIPTION OF THE INVENTION

In accordance with the present invention, the inventors have identified variants of HBV in patients chronically infected with HBV that were virologically non-responsive to ADF or ADF-comprising therapy and/or LAM or LAM-comprising therapy and/or a combination of these anti-HBV agents. Sequence analysis of isolated HBV DNA revealed the emergence of novel nucleic acid polymorphisms in the HBV polymerase. The occurrence of said polymorphism coincided with viral breakthrough persistence during nucleotide analogue therapy, a strong indication for the emergence/existence of adefovir-resistant HBV variants. In vitro findings confirmed that these HBV mutants are resistant to both adefovir and lamivudine even when treated with high concentrations of the nucleoside analogues.

More particularly, the present invention provides an improved diagnosis of the susceptibility of an HBV sample to antiviral drugs used to treat HBV infection and in a method and/or improved assay for the rapid and reliable detection of drug-induced mutations in the HBV genes allowing the simultaneous characterization of a range of codons involved in drug resistance which codons include the novel nucleic acid polymorphisms.

Throughout the invention as described below various publications are referenced. The contents of said publications are hereby incorporated by reference into the current application. Said publications are meant to describe more fully the art to which the current invention pertains.

A first aspect of the invention is related to isolated HBV variants that comprise at least one nucleotide mutation in the DNA polymerase gene, wherein said nucleotide mutation results in at least one amino acid substitution in domain B of the polymerase gene and wherein said variant exhibits a decreased sensitivity to a nucleoside analogue and/or other antiviral drugs against HBV. Preferred HBV variants comprise at least one nucleotide mutation that results in at least one amino acid substitution of the alanine at codon position 181 of the polymerase gene, more in particular at least one nucleotide mutation which results in an alanine to serine amino acid substitution at codon 181 of the polymerase gene, also indicated by rtA181S. The isolated HBV variant according to the invention preferably exhibits a decreased sensitivity to a nucleoside analogue, particularly the nucleoside analogue is Adefovir and/or Lamivudine.

The present invention also covers isolated HBV variants that comprise besides rtA181S further mutated genotypic patterns at other sites of the HBV polymerase. Preferably, the further mutation results in an altered amino acid sequence in any of the different domains of the polymerase gene. These include known amino acid alterations associated with drug resistance. Thus, the present invention extends to isolated HBV variants that comprise one rtA181S substitution in domain B of the polymerase gene and at least one further mutation coding for an amino acid substitution chosen from the group consisting of substitutions of leucine on position 180, methionine on position 204 and asparagine on position 236. Especially, the isolated variants comprise the result of rtA181S and rtM204I, or rtA181S and rtM204V, or rtA181S and rtM204S, or rtA181S and rtL180M, or rtA181S and rtN236T substitution.

The present invention also covers isolated HBV variants that comprise besides rtA181S further mutated genotypic patterns located in domain C of the polymerase gene. More preferably, the nucleotide substitution results in the substitution of the Methionine at codon position 204 in domain C of the polymerase gene. In particular covered are isolated HBV variants that comprises at least two nucleotide mutations in the DNA polymerase gene, wherein said nucleotide mutations result in at least two amino acid substitutions, one substitution of the alanine at codon position 181 in domain B of the polymerase and one substitution of the methionine at codon position 204 in domain C of the polymerase. The substitution of the methionine at codon position 204 is meant to include any amino acid other than methionine, preferably the subtitution is into an amino acid chosen from the group consisting of isoleucine and valine and serine.

The exemplary HBV variants comprise one rtA181S substitution in domain B of the HBV polymerase and one rtM204I substitution in domain C of the HBV polymerase. The isolated HBV variants of the present invention exhibit a decreased sensitivity to antiviral drugs against HBV, preferably to nucleoside analogues.

The term "mutation" has to be read in its broadest context and includes multiple mutations. It is to be understood that the present invention extends to isolated HBV variants that comprises at least one and/or two and/or three and/or four and/or five and/or six nucleotide mutations in the DNA polymerase gene, wherein said nucleotide mutations result in at least one and/or two and/or three and/or four and/or five and/or six amino acid substitutions, one substitution being the alanine at codon position 181 in domain B of the polymerase gene into any amino acid other than alanine, preferably the substitution of alanine into a serine.

"Isolated" when used in reference to the HBV variants and/or HBV polynucleic acids and/or expression products of this invention means that the variant or polynucleic acid have undergone at least one purification step away from naturally occurring body fluid and/or tissue or that it is not present in its native environment. Alternatively, the variants may be maintained in isolated body fluid and/or tissue or may be in a polynucleic acid form. Typically, this means that the virus variant or polynucleic acid is free of at least one of the host proteins and/or host nucleic acids. In general, the isolated virus variant or polynucleic acid is present in an in vitro environment. "Isolated" does not mean that the virus variant or polynucleic acid must be purified or homogeneous, although such preparations do fall within the scope of the term. "Isolated" simply means raised to a degree of purity, to the extent required excluding product of nature and accidental anticipations from the scope of the claims. "Isolated" is meant to include any biological material taken either directly from an infected human being or animal, or after culturing (enrichment). "Biological material" may be e.g. expectorations of any kind, broncheolavages, blood, skin tissue, biopsies, sperm, lymphocyte blood culture material, colonies, liquid cultures, faecal samples, urine, etc. "Biological material" may also be artificially infected cell cultures or the liquid phase thereof.

Reference to "decreased" or "reduced" sensitivity in relation to a nucleoside analogue includes and encompasses a complete or substantial resistance to the nucleoside analogue as well as partial resistance and includes a replication rate or replication efficiency which is more than a wild-type in the presence of a nucleoside analogue. In one aspect, this is conveniently measured by an increase in viral load during treatment, or alternatively, there is no substantial decrease in HBV DNA viral load from pre-treatment HBV DNA levels during treatment (i.e., non-response to treatment). Preferably, the "decreased sensitivity" is in respect of ADF. Alternatively, the "decreased sensitivity" is in respect of LAM. Alternatively, the "decreased sensitivity" is in respect of both LAM and ADF. Alternatively, the "decreased sensitivity" is in respect to ADF and/or LAM and/or other nucleoside analogs and/or other antiviral drugs against HBV. Many antiviral drugs against HBV (HBV antiviral drugs) are known and include: lobucavir, penciclovir or famciclovir, lamivudine (3TC; β-L-(−)-2',3'-dideoxy-3'-thiacytidine), interferon-α, adefovir dipivoxil (Bis-POM-PMEA) or adefovir (PMEA; 9-(2-phosphonyl-methoxyethyl)-adenine), entecavir (BMS 200475), emtricitabine [(−)FTC; (−)-β-L-2',3'-dideoxy-5-fluoro-3'-thiacytidine], DXG [(−)-β-D-2,6-diaminopurine dioxolane], DAPD (diaminopurine dioxolane), clevudine (L-FMAU; 2'-fluoro-5-methyl-β-L-arabinofuranosyluracil), L-dT (β-L-thymidine), L-Fd4C (2',3'-dideoxy-2',3'-didehydro-β-L(−)-5 fluorocytidine), foscarnet, carbovir, racivir, ganciclovir, tenofovir, nevirapine, (−)BCH189 (Ono et al., 2001), QYL865 (Fu et al., 2000), thymosin-α, and HBIg, the antibody against HBsAg. Two or more HBV antiviral drugs can be used in combination as well.

Not all HBV genomes have exactly the same length and the polymerase is likewise unequal, due to the presence of insertions or deletions within the linker or spacer domain between the terminal protein and catalytic components of the protein. To overcome this confusion, a group of investigators developed a genotype-independent numbering scheme for the polymerase. One possible way of indicating mutated codons in the HBV polymerase gene is according to Stuyver et al., 2001, where the methionine (M) in the YMDD locus of the catalytic C domain of polymerase is numbered rtM204 rather than 539, 549, 550 or 552. This numbering system will be used in the present patent application. Accordingly, mutations in the HBV DNA polymerase gene associated with nucleoside analogue treatment of chronic hepatitis B have been described in domain B as rtL180M and rtA181V, in domain C as rtM204I and rtM204V and in domain D as rtN236T.

Another aspect of the present invention relates to isolated polynucleic acids encoding the HBV variants of the present invention. These isolated polynucleic acids comprise a nucleotide mutation that results in at least one amino acid substitution and/or deletion in the HBV polymerase. In particular the invention relates to isolated polynucleic acids comprising a nucleotide mutation at codon 181 of the polymerase gene, more in particular comprising at least one nucleotide mutation which results in a substitution of alanine at codon 181 of the polymerase. More in particular the isolated polynucleic acids comprise a nucleotide mutation that results in an amino acid substitution rtA181S.

The present invention also covers isolated polynucleic acids that comprise besides rtA181S further mutated genotypic patterns at other sites of the HBV polymerase. Preferably, the further mutation results in an altered amino acid sequence in any of the different domains of the polymerase gene. These mutations include known amino acid alterations associated with drug resistance. Thus, the present invention extends to isolated polynucleic acids that comprise one mutation coding for the rtA181S substitution in domain B of the polymerase gene and at least one further mutation coding for an amino acid substitution chosen from the group of rtL180M, rtM204I or rtM204V or rtM204S and rtN236T.

The present invention also covers isolated polynucleic acids that comprise besides a mutation coding for rtA181S further mutated genotypic patterns located in domain C of the polymerase gene. More preferably, the further nucleotide mutation results in the substitution of the Methionine at codon position 204 in domain C of the polymerase gene. In particular isolated HBV variants are covered that comprises at least two nucleotide mutations in the DNA polymerase gene, wherein said nucleotide mutations result in at least two amino acid substitutions, one substitution of the alanine at codon position 181 in domain B of the polymerase gene and one substitution of the methionine at codon position 204 in domain C of the polymerase gene. The substitution of the methionine at codon position 204 is meant to include any amino acid other than methionine, preferably the substitution is into an isoleucine and/or a valine and/or a serine.

The exemplary polynucleic acids comprise nucleotide mutations in the DNA polymerase gene that code for the rtA181S substitution in domain B of the polymerase gene and for instance the rtM204I substitution in domain C of the polymerase gene. In a specific embodiment, said isolated HBV polynucleic acid comprises a sequence chosen from the group consisting of SEQ ID NO: 2, SEQ ID NO: 3, SEQ ID NO: 5, SEQ ID NO: 6 and SEQ ID NO: 7. More specifically, said isolated HBV polynucleic acid is defined by a sequence chosen from the group consisting of SEQ ID NO: 2, SEQ ID NO: 3, SEQ ID NO:5, SEQ ID NO:6 and SEQ ID NO:7.

Another aspect of the invention relates to fragments of the above-mentioned isolated polynucleic acid, which fragments comprise the described nucleotide mutations leading to a reduced sensitivity to a nucleoside analog and/or other anti-HBV agents. These fragments comprise at least the genotypic pattern that results in the rtA181S substitution.

In a further embodiment, said isolated HBV polynucleic acid thereof may be DNA, or RNA wherein T is replaced by U, or may be a synthetic polynucleic acid. Polynucleic acids encoding the variants of this invention vary in length and may vary in selection of bases flanking the mutant residue codon. The length of the polynucleic acid is not critical provided that it is recognized to be part of a hepatitis B virus sequence for the purpose intended. Considerable sequence variation exists within the genome of the virus, and thus the nucleic acid sequences flanking the variant sites may vary considerably even in the naturally occuring sequences. Sufficient polynucleic acid need only be present to provide novelty and utility for the sequence encoding the variant, but otherwise the length of the sequence flanking the selected codon is not important. Typically the length of the sequence (including the variant codon) will be any integer from within the range of 9 to 200 bp, usually 12, 13, 14, 15, 16, 17, 18, 19, 20, 21, 22, 23, 24, to 25 bp. Also included are sequences sufficiently long to encode the entire variants and fragments further described below.

The "isolated polynucleic acid or fragment thereof" according to the invention is meant to comprise single-stranded polynucleic acids, double-stranded polynucleic acids or triplex-forming polynucleic acids obtained directly from a sample or obtained after duplication, multiplication or amplification. "Obtained" is, in the present context, meant to include isolation and/or purification and/or amplification of said polynucleic acids from a biological sample. The "sample" may be any biological material taken either directly from an infected human being or animal, or after culturing (enrichment). "Duplication, multiplication or amplification" is meant to include any nucleic acid produced by using any nucleic acid amplification method including any sequencing technique. Thus, any sequencing technique producing a nucleic acid molecule comprising any of said, or a combination of said nucleic acid polymorphisms is to be understood to be comprised in the term "duplication, multiplication or amplification".

The term "synthetic polynucleic acid" as referred to here is meant to be a single-stranded polynucleic acid, double-stranded polynucleic acid or triplex-forming polynucleic acid. Polynucleic acids can be made in vitro by means of a nucleotide sequence amplification method. If such an amplified polynucleic acid is double-stranded, conversion to a single-stranded molecule can be achieved by a suitable exonuclease given that the desired single-stranded polynucleic acid is protected against said exonuclease activity. Alternatively, polynucleic acids are derived from recombinant plasmids containing inserts including the corresponding polynucleotide sequences, if need by cleaving the latter out from the cloned plasmids upon using the adequate nucleases and recovering them, e.g. by fractionation according to molecular weight. Another means of making a synthetic polynucleic acid in vitro is comprised within any method of nucleic acid sequencing. Products of a sequencing reaction are thus clearly covered by the term "synthetic polynucleic acid". The polynucleic acids according to the present invention can also be synthesized chemically, for instance by applying the conventional phospho-triester or phosphoramidite chemistry.

"Nucleotide sequence (DNA or RNA) amplification" is meant to include all methods resulting in multiplication of the number of target nucleotide sequence copies. Nucleotide sequence amplification methods include the polymerase chain reaction (PCR; DNA amplification), strand displacement amplification (SDA; DNA amplification), transcription-based amplification system (TAS; RNA amplification), self-sustained sequence replication (3SR; RNA amplification), nucleic acid sequence-based amplification (NASBA; RNA amplification), transcription-mediated amplification (TMA; RNA amplification), Qβ-replicase-mediated amplification and run-off transcription.

The terms "polynucleotide", "polynucleic acid", "nucleic acid sequence", "nucleotide sequence", "nucleic acid molecule", "oligonucleotide", "probe" or "primer", when used herein refer to nucleotides, either ribonucleotides, deoxyribonucleotides, peptide nucleotides or locked nucleotides, or a combination thereof, in a polymeric form of any length or any shape (e.g. branched DNA). Said terms furthermore include double-stranded (ds) and single-stranded (ss) polynucleotides as well as triple-stranded polynucleotides. Said terms also include known nucleotide modifications such as methylation, cyclization and 'caps' and substitution of one or more of the naturally occurring nucleotides with an analog such as inosine or with nonamplifiable monomers such as HEG (hexethylene glycol).

Ribonucleotides are denoted as NTPs, deoxyribonucleotides as dNTPs and dideoxyribonucleotides as ddNTPs.

Nucleotides can generally be labeled radioactively, chemiluminescently, fluorescently, phosphorescently or with infrared dyes or with a surface-enhanced Raman label or plasmon resonant particle (PRP).

Modifications of nucleotides include the addition of acridine or derivatives thereof, Acrydite™, amine, biotin, BHQ-1™, BHQ-2™, BHQ-3™, borane dNTPs, carbon spacers (e.g. $C_3$, $C_6$, $C_7$, $C_9$, $C_{12}$ or $C_{18}$), cascade blue, cholesterol, coumarin or derivatives thereof, Cy3®, Cy3.5®, Cy5®, Cy5.5®, Cy7® DABCYL, dansylchloride, digoxigenin, dinitrophenyl, dual biotin, EDANS, 6-FAM, fluorescein, 3'-glyceryl, HEX, IAEDANS, inverted dA, inverted dG, inverted dC, inverted dG, IRD-700, IRD-800, JOE, La Jolla Blue, metal clusters such as gold nanoparticles, phenylboronic acid, phosphate psoralen, 3'- or 5'-phosphorylation, pyrene, 3' riboadenosine, 3' ribo-guanosine, 3' ribo-cytidine, (LC)Red640, (LC)Red705, rhodamine, ROX, thiol (SH), spacers, TAMRA, TET, AMCA-S®, SE, BODIPY®, Marina Blue®, Oregon Green®, Pacific Blue®, QSY7™, Rhodamine Green®, Rhodamine Red®, Rhodol Green®, tetramethylrhodamine, Texas Red®, Uni-Link $NH_2$-modifier, radiolabels (e.g. $^{125}I$, $^{131}I$, $^{35}S$, $^{14}C$, $^{32}P$, $^{33}P$, $^{3}H$) and nanoparticles.

Polynucleotide backbone and base modifications further include 2'-deoxyaristero-mecyin, methylphosphonate, 2'-OMe-methylphosphonate RNA, 2'-O-(2-methoxyethyl), phosphorothioate, alkylphosphorothiate, phosphoramidite, RNA, 2'-OMeRNA, 2-amino-dA, 2-aminopurine, 3'-(ddA), 3'dA(cordycepin), 7-deaza-dA, 8-Br-dA, 8-oxo-dA, $N^6$-Me-dA, abasic site (dSpacer), biotin dT, 2'-OMe-5Me-C, 2'-OMe-propynyl-C, 3'-(5-Me-dC), 3'-(ddC), 5-Br-dC, 5-I-dC, 5-Me-dC, 5-F-dC, carboxy-dT, convertible dA, convertible dC, convertible dG, convertible dT, convertible dU, 7-deaza-dG, 8-Br-dG, 8-oxo-dG, $O^6$-Me-dG, S6-DNP-dG, 4-methyl-indole, 5-nitroindole, 2'-OMe-inosine, 2'-dI, $O^6$-phenyl-dI, 4-methyl-indole, 2'-deoxynebularine, 5-nitroindole, 2-aminopurine, dP(purine analogue), dK(pyrimidine analogue), 3-nitropyrrole, 2-thio-dT, 4-thio-dT, biotin-dT, carboxy-dT, $O^4$-Me-dT, $O^4$-triazol dT, 2'-OMe-propynyl-U, 5-Br-dU, 2'-dU, 5-F-dU, 5-I-dU, $O^4$-triazol dU.

Further modifications of polynucleotides include hapten- or protein-labeling. Haptens include e.g. biotin and digoxigenin whereas proteins include enzymes such as soybean or horseradish peroxidase, β-galactosidase, luciferase, alkaline phosphatase, glutathione S-transferase or dihydrofolate reductase or may constitute heterologous epitopes such as (histidine)$_6$-tag, protein A, maltose-binding protein, Tag•100 epitope (EETARFQPGYRS; SEQ ID NO:15), c-myc epitope (EQKLISEEDL; SEQ ID NO:16), FLAG®-epitope (DYKD-DDK; SEQ ID NO:17), lacZ, CMP (calmodulin-binding peptide), HA epitope (YPYDVPDYA; SEQ ID NO:18), protein C epitope (EDQVDPRLIDGK; SEQ ID NO:19) and VSV epitope (YTDIEMNRLGK; SEQ ID NO:20). Other proteins include histones, single-strand binding protein (ssB) and native and engineered fluorescent proteins such as green-, red-, blue-, yellow-, cyan-fluorescent proteins. Crosslinking moieties can also be incorporated such as coumarins, furocoumarins or benzodipyrones, or derivates of any thereof.

In a further embodiment said terms "polynucleotide", "polynucleic acid", "nucleic acid sequence", "nucleotide sequence", "nucleic acid molecule", "oligonucleotide", "probe" or "primer" also encompass peptide nucleic acids (PNAs), a DNA analogue in which the backbone is a pseudopeptide consisting of N-(2-aminoethyl)-glycine units rather than a sugar. PNAs mimic the behavior of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors. PNA probes can generally be shorter than DNA probes and are generally from 6 to 20 bases in length and more optinally from 12 to 18 bases in length (Nielsen, 2001).

In a further embodiment said terms further encompass locked nucleic acids (LNAs) which are RNA derivatives in which the ribose ring is constrained by a methylene linkage between the 2'-oxygen and the 4'-carbon. LNAs display unprecedented binding affinity towards DNA or RNA target sequences. LNA nucleotides can be oligomerized and can be incorporated in chimeric or mix-meric LNA/DNA or LNA/RNA molecules. LNAs seem to be nontoxic for cultured cells (Orum et al., 2001; Wahlestedt et al., 2000). In general, chimeras or mix-mers of any of DNA, RNA, PNA and LNA are considered as well as any of these wherein thymine is replaced by uracil.

The term "nucleic acid polymorphism" or "nucleotide sequence polymorphism" is meant to include any difference in the primary nucleotide sequence of the nucleic acid under investigation relative to the primary nucleotide sequence of one or more reference nucleic acids. The most simple nucleic acid polymorphism is a polymorphism affecting a single nucleotide, i.e. a single nucleotide polymorphism or SNP. Nucleic acid polymorphisms further include any number of contiguous and/or non-contiguous differences in the primary nucleotide sequence of the nucleic acid under investigation relative to the primary nucleotide sequence of one or more reference nucleic acids. The above explanation also clarifies terms like "polymorphic variant".

An assessment of a potential viral variant is important for the selection of an appropriate therapeutic protocol. Such an assessment is suitably facilitated with the assistance of a computer programmed with software. Thus, in yet another embodiment, said isolated HBV polynucleic acid sequences or fragments thereof, or the amino acid sequences derived thereof, may be in ASCII-, hexadecimal- or UNICODE code, in a single-byte, double-byte or multiple-byte character set or in a binary code. In an additional embodiment, said sequences in ASCII-, hexadecimal- or UNICODE code, in a single-, double- or multi-byte character set or in binary code are readable by a computer. In a further embodiment, said sequences in ASCII-, hexadecimal- or UNICODE code, in a single-, double- or multi-byte character set or in binary code are recordable on a computer readable carrier or are incorporatable in a computer-readable database. In yet another embodiment is covered computer readable carriers comprising said sequences in ASCII-, hexadecimal- or UNICODE code, in a single-, double- or multi-byte character set or in binary code. In yet another further embodiment of the invention is envisaged a computer readable database comprising said sequences in ASCII-, hexadecimal- or UNICODE code, in a single-, double- or multi-byte character set or in binary code. In yet another further embodiment, said sequences in ASCII-, hexadecimal- or UNICODE code, in a single-, double- or multi-byte character set or in binary code is used in algorithms capable of comparing sequences or capable of aligning sequences.

In a further aspect of the present invention is comprised a vector comprising the isolated HBV polynucleic acid or fragment thereof according to the invention. In a specific embodiment, said vector is an expression vector. In another specific embodiment, said vector is a viral or a retroviral vector.

In a further embodiment, said vector is a universal cloning vector such as the pUC-series or pEMBL-series vectors or cloning vectors such as cloning vectors requiring a DNA topoisomerase reaction for cloning, TA-cloning vectors and recombination-based cloning vectors such as those used in the Gateway system (InVitrogen). Vectors comprise plasmids, phagemids, cosmids or bacmids (baculovirus vectors). A vector can merely function as a cloning tool and/or—vehicle or may additionally comprise regulatory sequences such as promoters, enhancers and terminators or polyadenylation signals. Said regulatory sequences may enable expression of the information contained within the DNA fragment of interest cloned into a vector comprising said regulatory sequences. Expression may be the production of RNA molecules or mRNA molecules and, optionally, the production of protein molecules thereof. Expression may be the production of an RNA molecule by means of a viral polymerase promoter (e.g. SP6, T7 or T3 promoter) introduced to the 5'- or 3'-end of the DNA of interest.

Expression may furthermore be transient expression or stable expression or, alternatively, controllable expression. Controllable expression comprises inducible expression, e.g. using a tetracyclin-regulatable promoter, a stress-inducible (e.g. human hsp70 gene promoter), a methallothionine promoter, a glucocorticoid promoter or a progesterone promoter. Promoters further include HBV promoters such as the core promoter and heterologous promoters such as the cytomegalovirus (CMV) immediate early (IE) promoter.

A promoter can also preferably drive expression in liver tumour cells, e.g. the promoter and enhancer of the α-foetoprotein gene. Expression vectors are known in the art that mediate expression in bacteria (e.g. *Escherichia coli, Streptomyces* species), fungi (e.g. *Saccharomyces cerevisiae, Schizosaccharomyces pombe, Pichia pastoris, Aspergillus* species, *Hansenula polymorpha, Neurospora crassa*), insect cells (*Spodoptera frugiperda* cells, Sf9 cells), plant cells (e.g. potato virus X-based expression vectors, see e.g. Vance et al. 1998 in International Patent Publication No WO 98/44097) and mammalian cells (e.g. CHO or COS cells, Vero cells, cells from the HeLa cell line). Particularly suited host cells in the context of the present invention are mammalian, e.g. human, primary hepatocytes, hepatoma cell lines (e.g. HepG2, HepT1, HepT3, Huh6, Huh7), Chang liver cells, rodent liver cells, primate liver cells, hominoid liver cells, or any other mammalian, e.g. human, host cells or cell line.

A vector, or an expression vector, may furthermore be capable of autonomous replication in a host cell or may be an integrative vector, i.e. a vector completely or partially, and stably, integrating in the genome of a host cell. Integration of any first DNA fragment, e.g. a vector or a fragment thereof, in any other second DNA fragment, e.g. the genome of a host cell, can be reversed if said first DNA fragment is flanked e.g. by site-specific recombination sites or by repeat sequences typical for transposons. Alternatively, said site-specific recombination sites or transposon-repeat sequences are comprised in said second DNA fragment and are flanking said first DNA fragment. In yet another alternative, said first DNA fragment can possibly be introduced in a thereto suitable second DNA fragment by homologous recombination and the same process can be used to exchange said first DNA fragment with another thereto suitable DNA fragment.

Introduction of a vector, or an expression vector, into a host cell may be effectuated by any available transformation or transfection technique applicable to said host cell as known in the art. Such transformation or transfection techniques comprise heat-shock mediated transformation (e.g. of *E. coli*), conjugative DNA transfer, electroporation, PEG-mediated DNA uptake, liposome-mediated DNA uptake, lipofection, calcium-phosphate DNA coprecipitation, DEAE-dextran mediated transfection, direct introduction by e.g. microinjection or particle bombardment, or introduction by means of a virus, virion or viral particle.

Infection of e.g. HepG2 cell cultures by HBV viruses (e.g. derived from a patient's serum or from a cell culture) is normally not occurring but may be stimulated by pretreatment of the host cells with dimethylsulfoxide (DMSO; (Paran et al., 2001)). Alternatively, digestion of HBV with V8 protease results in infectious HBV viruses (Lu et al., 1996). A similar protease modification of at least one other hepadnavirus, woodchuck hepatitis virus (WHV), likewise results in WHV viruses which are infectious for human hepatoblastoma cells (Lu et al., 2001). Expression of HBV genes in hepatoblastoma cells was reported to increase significantly by lowering the incubation temperature from 37° C. to 32° C. (Kosovsky et al., 2000).

Vectors suited for assaying viral replication efficiency, more particularly for assaying HBV replication efficiency, include viral vectors or vectors comprising at least 1 unit (full-length) HBV genome, preferably greater than 1 unit HBV genome, e.g. 1.1-4, in particular 1.1, 1.2, 1.28, 1.3, 1.4, 1.5, 1.6, 1.7, 1.8, 1.9, 2.0, 3.0 or 4.0 times the HBV genome. One example of a viral vector system enabling HBV viral replication is a baculovirial system, e.g. as described by Isom and Harriet in International Patent Publication No WO99/37821 or by Delaney et al. (Delaney et al., 1999). The extent of viral replication can be monitored by measuring or detecting either one or more of (i) secrection of an HBV antigen (HBsAg or HBeAg), (ii) expression of HBV transcripts (3.5 kb-, 2.4 kb-, 2.1 kb-, 0.7 kb-transcripts), (iii) the amount of HBV replicative intermediates (relaxed circular DNA, double stranded DNA or single stranded DNA), (iv) the amount of HBV supercoiled circular (ccc) DNA, (v) the amount of secreted extracellular HBV DNA, (vi) the amount of extracellularly produced HBV particles, (vii) the amount of produced HBcAg protein, (viii) the amount of produced HBV DNA polymerase/reverse transcriptase protein, and (ix) the amount of produced HBV X protein. Another example of a viral vector system enabling HBV viral replication is a vector system which includes an indicator gene (e.g. a selectable marker gene or a screenable marker gene; e.g. as described by Capon and Petropoulos in U.S. Pat. No. 6,242,187), the expression of which is indicative for the extent of viral replication.

Viral vector systems enabling HBV viral replication are suited to compare replication efficiency of wild-type HBV viruses with replication efficiency of mutant HBV viruses. Mutant HBV viruses are understood to be HBV viruses comprising a mutation or a polynucleic acid polymorphism in either one or more of the HBV ORFs and/or the HBV regulatory sequences (e.g. promoter, enhancer, terminator or polyadenylation signal, epsilon-loop, encapsidation signal, repeat sequence, packaging signal, internal ribosome entry site).

A further aspect of the invention relates to a host cell comprising an HBV polynucleic acid or fragment thereof according to the invention, or comprising an HBV DNA polymerase/reverse transcriptase protein or fragment thereof according to the invention, or comprising an HBV variant according to the invention, or comprising a vector according to the invention. In a specific embodiment, said host cell is a mammalian liver cell or a mammalian hepatoma cell as described supra.

The present invention further relates to expression products from the isolated polynucleic acids. These expression products result from the expression of any of the polynucleic acids and/or fragments described supra.

Said expression products comprise proteins, peptides, oligopeptides, RNA or mRNA. The terms "protein", "peptide" or "oligopeptide", when used herein refer to amino acids in a polymeric form of any length. Said terms also include known amino acid modifications such as disulphide bond formation, cysteinylation, oxidation, glutathionylation, methylation, acetylation, farnesylation, biotinylation, stearoylation, formylation, lipoic acid addition, phosphorylation, sulphation, ubiquitination, myristoylation, palmitoylation, geranylgeranylation, cyclization (e.g. pyroglutamic acid formation), oxidation, deamidation, dehydration, glycosylation (e.g. pentoses, hexosamines, N-acetylhexosamines, deoxyhexoses, hexoses, sialic acid etc.) and acylation as well as non-naturally occurring amino acid residues, L-amino acid residues and D-amino acid residues. A number of said amino acid modifications can occur as a result of post-translational modification as will be recognized by the one skilled in the art. Other modifications include the addition of a chemical group to one or more amino acids of a protein, peptide or oligopeptide. Said chemical groups include e.g. biotin. Proteins, peptides or oligopeptides can furthermore generally be labeled radioactively, chemiluminescently, fluorescently, phosphorescently, with infrared dyes or with a surface-enhanced Raman label or plasmon resonant particle.

The present invention extends to expression products that comprise at least one amino acid substitution and/or deletion in the polymerase gene. In particular the invention relates to expression products comprising an amino acid substitution at codon 181 of the polymerase gene, more in particular the one that results in an alanine to serine amino acid substitution at codon 181 of the polymerase gene. More in particular the expression product comprises the amino acid substitution rtA181S.

The present invention also covers expression products that comprise besides rtA181S further amino acid substitutions located in domain C of the polymerase. More preferably, the substitution of the Methionine at codon position 204 in domain C of the polymerase. In particular covered are expression products that comprise at least two amino acid substitutions in the DNA polymerase, one substitution of the alanine into serine at codon position 181 in domain B of the polymerase gene and one substitution of the methionine at codon position 204 in domain C of the polymerase gene. The substitution of the methionine at codon position 204 is meant to include any amino acid other than methionine, preferably the substitution is into an isoleucine or a valine or a serine.

The present invention also covers expression products that comprise besides rtA181S further amino acid substitutions at other sites of the HBV polymerase, preferably at least one amino acid substitution chosen from the group of rtL180M, rtM204I or rtM204V or rtM204S and rtN236T. The different mutations at codon 204 within a group has been indicated by twice "or".

Exemplary expression products comprise the rtA181S substitution in domain B of the polymerase optionally with the rtM204I substitution in domain C of the polymerase. In a specific embodiment, said isolated HBV expression products comprise a sequence chosen from the group consisting of SEQ ID NO: 10, SEQ ID NO: 11, SEQ ID NO: 13 and SEQ ID NO: 14. More specifically, said isolated HBV polynucleic acid is defined by a sequence chosen from the group consisting of SEQ ID NO: 10, SEQ ID NO: 11, SEQ ID NO: 13 and SEQ ID NO:14.

Another aspect of the invention relates to fragments of the above-mentioned expression products, which fragments comprise the described amino acid substitutions leading to a reduced sensitivity to a nucleoside analog and/or other anti-HBV agents. These fragments comprise at least the rtA181S substitution.

The expression products comprise polypeptides that include full-length hepatitis B polymerase and/or reverse transcriptase and fragments thereof comprising at least the mutant residue or site, and/or either of these fused to a heterologous polypeptide.

Expression includes the production of RNA molecules or mRNA molecules comprising the disclosed mutated genotypic patterns. "Heterologous" when used in reference to polynucleic acid or protein sequences does not mean the same as native or known flanking sequences. Heterologous sequences include other HBV, human animal or microbial sequences, polyHis or other affinity tags, or entirely fabricated sequences. Fragments typically will include the variant residue plus at least about 4 total flanking residues apportioned to either or both flanks of the mutant residue, usually 10 to 20 residues in total.

The present invention further embraces the aspect of oligonucleotides capable of discriminating, in an HBV polynucleic acid or fragment thereof according to the invention, a serine-encoding codon 181 in the HBV reverse transcriptase domain from a codon 181 encoding an alanine or a valine in the HBV reverse transcriptase domain.

The term "oligonucleotide" as referred to herein is meant to be a primer or a probe and may be single-stranded or double-stranded or may be part of a triplex-forming polynucleic acid. Oligonucleotides can be made in vitro by means of a nucleotide sequence amplification method. If such an amplified oligonucleotide is double-stranded, conversion to a single-stranded molecule can be achieved by a suitable exonuclease given that the desired single-stranded oligonucleotide is protected against said exonuclease activity. Alternatively, oligonucleotides are derived from recombinant plasmids containing inserts including the corresponding nucleotide sequences, if need be by cleaving the latter out from the cloned plasmids upon using the adequate nucleases and recovering them, e.g. by fractionation according to molecular weight. The oligonucleotides according to the present invention can also be synthetic, i.e. be synthesized chemically, for instance by applying the conventional phospho-triester or phosphoramidite chemistry. Oligonucleotides can further be synthesized in situ on a glass slide via solid-phase oligonucleotide synthesis or via photolitographic synthesis (Beaucage, 2001).

In another specific embodiment, the oligonucleotide according to the present invention further comprises a modification for attaching said oligonucleotide to a solid support. Said modification may for instance be an amine-, thiol-, 3-'propanolamine or Acrydite-modification of the oligonucleotide or may comprise the addition of a homopolymeric tail (e.g. an oligo(dT)-tail added enzymatically via a terminal transferase enzyme or added synthetically) to the oligonucleotide. If said homopolymeric tail is positioned at the 3'-terminus of the oligonucleotide or if any other 3'-terminal modification preventing enzymatic extension is incorporated in the oligonucleotide, the priming capacity of the oligonucleotide can be decreased or abolished. Other modifications are described in e.g. (Beaucage, 2001). Clearly, oligonucleotides according to the present invention which are DNA, RNA, PNA or LNA, or which are any chimaera thereof are embodied in the invention. Further embodied are compositions comprising at least one oligonucleotide according to the invention. "Hybridization" is the process wherein substantially homologous complementary nucleotide sequences anneal to each other. The hybridization process can occur entirely in solution, i.e. both complementary nucleic acids are in solution. Tools in molecular biology relying on such a process include PCR, subtractive hybridization and DNA sequence determination. The hybridization process can also occur with one of the complementary nucleic acids immobilized to a matrix such as magnetic beads, Sepharose beads or any other resin or type of beads. Tools in molecular biology relying on such a process include the isolation of poly (A$^+$) mRNA. The hybridization process can furthermore occur with one of the complementary nucleic acids immobilized to a solid support such as a nitrocellulose or nylon membrane, a glass slide or fused silica (quartz) slide (the latter known as nucleic acid arrays or microarrays or as nucleic acid chips), a gold film, a polypyrrole film, an optical fiber or in e.g. a polyacrylamide gel or a microplate well. Tools in molecular biology relying on such a process include RNA and DNA gel blot analysis, colony hybridization, plaque hybridization, reverse hybridization and microarray hybridization. In order to allow hybridization to occur, the nucleic acid molecules are generally thermally, chemically (e.g. by NaOH) or electrochemically denatured to melt a double strand into two single strands and/or to remove hairpins or 'Molecular Beacons' probes (single dual-labeled) or other secondary structures from single stranded nucleic acids.

The nucleic acid sequences of the invention may furthermore be linked to an external guide sequence (EGS) or a short external guide sequence (eSEGS). Said guide sequences linked to a target sequence provide a minimal structure that is recognized as a substrate by RNAse P enzymes (Werner and George in U.S. Pat. No. 5,877,162). Nucleic acid sequences of the invention linked to an EGS or a SEGS may find therapeutic applications in treating HBV-infected patients.

Further aspects of the present invention are methods for detecting the presence of an HBV virus in a biological sample; and/or for detecting resistance to an antiviral drug of an HBV virus present in a biological sample; and/or for detecting the presence of a serine-encoding codon 181, or of a serine-encoding codon 181 and a codon chosen from the group consisting of a methionine-encoding codon 180, an isoleucine-encoding codon 204, a valine-encoding codon 204, a serine-encoding codon 204, and a threonine-encoding codon 236 in the HBV reverse transcriptase domain an HBV virus present in a biological sample.

With "codon" is meant a combination of 3 contiguous nucleotides that encode an amino acid according to the genetic code. A "codon" in the present invention furthermore can be comprised in a single-stranded (sense or antisense) or double-stranded (poly)nucleic acid. For deriving the amino acid sequence from an antisense strand, the corresponding sense strand (the inverted complement) needs to be used for translation into the corresponding amino acid sequence.

A large number of assays capable of detecting nucleotide sequences and nucleotide sequence polymorphisms (e.g. a mutation) is currently available. Some of these assays are based on physical methods whereas others use enzymatic approaches.

With "physical detection methods" is meant in the present context methods of nucleotide sequence polymorphism detection that require one or more physical processes for detection although not excluding the enzymatic process of prior PCR amplification of the target DNA sequence comprising one or more nucleotide sequence polymorphisms. Said physical processes include electrophoresis, chromatography, spectrometry, optical signal sensing and spectroscopy.

Physical nucleotide sequence polymorphism detection assays include electrophoretic methods such as single stranded conformation polymorphism (SSCP), constant denaturant capillary electrophoresis (CDCE) and constant denaturant gel electrophoresis (CDGE) see for instance Kristensen et al., 2001; denaturing gradient gel electrophoresis (DGGE), double gradient capillary electrophoresis (DGCE), capillary zone electrophoresis (CZE) is also known as free-solution capillary electrophoresis (FSCE), nonisocratic CZE, or thermal gradient capillary electrophoresis (TGCE), two-dimensional gene scanning (TDGS), conformation sensitive gel electrophoresis (CSGE), see for instance Korkko et al., 1998, microplate-array diagonal gel electrophoresis (MADGE), see for instance Day et al., 1998 and double-strand conformation analysis (DSCA), see for instance (Arguello et al., 1998). A similar technique is called HMA (heteroduplex mobility assay) but detection of DNA-duplexes relies on in gel staining of the DNA (Delwart et al., 1993). In HTA (heteroduplex tracking assay), a radiolabeled probe is annealed to a PCR product and the probe-PCR product heteroduplexes are separated by gel electrophoresis. A multiple-site-specific HTA has been described (Resch et al., 2001; Delwart et al., 1994).

Double-strand conformation analysis chromatographic methods include denaturing high-performance liquid chromatography (DHPLC). Physical nucleotide sequence polymorphism detection assays may be effective for identification of known or new mutations and may require confirmation by direct DNA sequencing resulting in separation of homo- and heteroduplex target DNA molecules by denaturing electrophoresis. Said separation can also be performed by denaturing liquid chromatography wherein temperature determines sensitivity. DHPLC can moreover be performed in monolithic capillary columns enabling the setting up of an array system. Fluorescence-based detection is possible, as well as on-line coupling to a mass spectrometer. The efficiency of nucleotide polymorphism detection by DHPLC can be increased by adding a GC-clamp to the end of the target DNA fragment (Huber et al., 2001; Narayanaswami et al., 2001; Xiao et al., 2001).

MALDI-TOF MS (matrix-assisted laser desorption-ionization time-of-flight mass spectrometry) has been successfully used both as a direct DNA sequencing tool for DNA fragments under 100 bp and as a tool for detection of single nucleotide polymorphisms. Hybridization of allele-specific PNA-oligomers (peptide nucleic acid) with single stranded target DNA was proven to be highly compatible with MALDI-TOF MS analysis ((Griffin et al., 2000), and references therein).

Still regarded as the 'gold standard' for determination of nucleotide sequence polymorphisms is direct DNA sequencing as for instance designed by Maxam and Gilbert (Maxam et al., 1977). The most common and widespread DNA sequencing method is based on the Sanger reaction or dideoxynucleotide chain termination reaction (Sanger et al., 1977). Sequencing primers can be labeled for detection of the terminated chains or internal labeling of the extension product is possible. Other DNA sequencing methods are pyrosequencing (see e.g. Williams 2000) and cycle sequencing (Yager et al., 1999; Ruano et al., 1991).

In the near future, nanopore sequencing might also become available (Meller et al., 2000). Other DNA sequencing methods include molecular resonance sequencing and diagnostic sequencing by combining specific cleavage of DNA followed by mass spectrometric analysis of the fragments (see e.g. Stanssens and Zabeau 2000—WO00/66771).

Another method of determining nucleotide sequence variations comprises dideoxynucleotide sequencing (Sanger reaction) wherein the regular dNTPs are replaced by modified dNTPs (such as α-thio dNTPs) and other variants (Dahlhauser 2000—U.S. Pat. No. 6,150,105).

Yet another DNA sequencing methodology is known as SBH or sequencing-by-hybridization which uses an array of all possible n-nucleotide oligomers (n-mers) to identify n-mers comprised in an unknown DNA sample (Drmanac et al., 1993).

Said high-density oligonucleotide arrays or DNA chips abolish the need to design a set of oligonucleotides specifically hybridizing under the same conditions to a set of polymorphic nucleotide sequences. The latter approach is applied in conventional reverse blot assays by carefully adjusting length, polarity and position of the mismatched nucleotide(s) in the oligonucleotide probe (Saiki et al., 1989). Conventional reverse blot hybridization assays for genotyping and detection of nucleotide sequence polymorphisms have, however, been successfully commercialized, e.g. in the LiPA (Line Probe Assay) format (Innogenetics, Ghent, Belgium). (Stuyver et al., 1997; Stuyver et al., 1996).

It will be clear to the skilled artisan that many variations and combinations can be made to the nucleotide sequence and nucleotide sequence polymorphism detection methods described supra. These are hereby incorporated in the present invention.

The oligonucleotides according to the invention as described supra can be adapted such that they can be used in any of the methods for detection of nucleotide sequences or polymorphisms therein as described supra.

Thus, in an additional embodiment of the present invention, the oligonucleotide according to the invention further comprises a terminal extension and/or a hairpin or 'Molecular Beacons' probe structure, wherein said extension and/or hairpin structure is incorporated at either end or at both ends of said oligonucleotide. Said terminal extension is useful for, e.g., specifically hybridizing with another nucleic acid molecule, and/or for facilitating attachment of said oligonucleotide to a solid support, and/or for modification of said tailed oligonucleotide by an enzyme, ribozyme or DNAzyme.

In a further embodiment of the current invention, the oligonucleotide according to the invention is comprised within a padlock probe that incorporates at either end primers which, after annealing to a target DNA, can be ligated, or within a hairpin structure.

In another embodiment, the oligonucleotide of the present invention has a modification allowing detection and/or capturing of said oligonucleotide. Detection and/or capturing of said oligonucleotide furthermore enables detection and/or capturing of the target nucleic acid hybridized therewith. The interaction between said oligonucleotide and said target nucleic acid may be stabilized by cross-linking both via introduction of a cross-linking modification in said oligonucleotide and/or said target nucleic acid.

In yet another embodiment, the oligonucleotide of the invention comprises a 3'-terminal mismatching nucleotide and, optionally, a 3'-proximal mismatching nucleotide. Said oligonucleotides are particularly useful for performing polymorphism-specific PCR and LCR (Ligase Chain Reaction) or GAP-LCR.

Further comprised in the present invention is a composition comprising at least one oligonucleotide according to the description given supra.

It will be clear to the skilled artisan that any of the methods described supra for detecting nucleotide sequences and polymorphisms therein can be utilized for methods for detecting the presence of an HBV virus in a biological sample; and/or for detecting resistance to an antiviral drug of an HBV virus present in a biological sample; and/or for detecting the presence of a serine-encoding codon 181, or of a serine-encoding codon 181 and a codon chosen from the group consisting of a methionine-encoding codon 180, an isoleucine-encoding codon 204, a valine-encoding codon 204, a serine-encoding codon 204, and a threonine-encoding codon 236 of the HBV reverse transcriptase domain of an HBV virus present in a biological sample.

Therefore, the following aspects covering such detection methods and diagnostic kits, e.g. line probe assays, based on such detection methods are additionally included in the present invention.

One aspect of the invention relates to a method for detecting the presence of an HBV virus in a biological sample and/or a method for detecting resistance to an antiviral drug of an HBV virus present in a biological sample, said methods comprising the step of detecting the presence of an HBV polynucleic acid or fragment thereof according to the invention. A specific embodiment thereto includes said method comprising the steps of:

a. obtaining a target HBV polynucleic acid from said biological sample wherein said target HBV polynucleic acid is suspected to comprise a serine-encoding codon 181 of the HBV reverse transcriptase domain, and optionally one or more of the codons chosen from the group consisting of a methionine-encoding codon 180, an isoleucine-encoding codon 204 or a valine-encoding codon 204 or a serine-encoding codon 204, and a threonine encoding codon 236 of the HBV reverse transcriptase domain of an HBV virus;

b. obtaining the nucleic acid sequence of the target HBV polynucleic acid of (a);

c. infering, from the nucleic acid sequence obtained in (b), the presence of said serine-encoding codon 181 of the HBV reverse transcriptase domain, and optionally one or more codons chosen from the group mentioned in (a)

and, therefrom, the presence of said HBV virus in said biological sample and/or said resistance to an antiviral drug of an HBV virus present in said biological sample.

Another specific embodiment thereto includes said methods comprising:
a. obtaining a target HBV polynucleic acid present in said biological sample and/or obtaining the nucleotide sequence thereof;
b. when appropriate, partially or completely denaturing, or enzymatically modifying the polynucleic acids obtained in step (a);
c. when appropriate, renaturating the denatured polynucleic acids obtained in step (b), preferably in the presence of at least one oligonucleotide capable of discriminating, in an HBV polynucleic acid or a fragment thereof a serine-encoding codon 181 in the HBV reverse transcriptase domain from a codon 181 encoding an alanine or a valine in the HBV reverse transcriptase domain, and, if needed, including the step of enzymatically modifying, including extending, said oligonucleotide;
d. when appropriate, detection of the partially or completely denatured HBV polynucleic acids obtained in step (b), and/or of the hybrids formed in step (c), and/or of the enzymatic modifications obtained in step (b) and/or (c);
e. infering from one or more of the data of the following groups: the partially or completely denatured polynucleic acids, the hybrids, the enzymatic modifications, all detected in step (d), and from the nucleotide sequence obtained in (a), the presence of said HBV in said biological sample and/or said resistance to an antiviral drug of an HBV present in said biological sample.

In yet another specific embodiment thereto, said method comprising:
a. obtaining a target HBV polynucleic acid from said biological sample wherein said target HBV polynucleic acid is suspected to comprise a serine-encoding codon 181 of the HBV reverse transcriptase domain, optionally together with one or more of the codons chosen from the group consisting of a methionine-encoding codon 180, an isoleucine-encoding codon 204 or a valine-encoding codon 204 or a serine-encoding codon 204, and a threonine encoding codon 236 of the HBV reverse transcriptase domain of an HBV;
b. contacting the target HBV polynucleic acid of (a) with an oligonucleotide capable of discriminating a codon 181 encoding a serine from a codon 181 encoding an alanine or valine, and optionally also capable of discriminating one or more codons chosen from the group consisting of a codon 180 encoding a leucine from a codon 180 encoding a methionine, a codon 204 encoding an isoleucine from a codon 204 encoding a methionine, valine or serine, and a codon 236 encoding an asparagine from a codon 236 encoding a threonine;
c. infering, from the discriminatory signal obtained in (b), the presence of said serine-encoding codon 181 of the HBV reverse transcriptase, optionally together with said methionine-encoding codon 180 or said isoleucine-encoding codon 204 or said asparagine-encoding codon 236 of the HBV reverse transcriptase domain and, therefrom, the presence of said HBV in said biological sample and/or said resistance to an antiviral drug of an HBV virus present in said biological sample.

In the latter methods, said discriminating in (b) is generally based on hybridization and said discriminatory signal in (c) is a hybridization signal.

With an "oligonucleotide capable of discriminating, in a (poly)nucleic acid, a codon encoding amino acid X1 (any amino acid) from a codon encoding amino acid X2 (any amino acid different from X1)" is meant an oligonucleotide yielding a signal when contacted with a (poly)nucleic acid comprising said codon encoding amino acid X1 but not yielding a signal when contacted with a (poly)nucleic acid comprising a codon encoding amino acid X2. Said signal, also referred to as "discriminatory signal", may be any signal obtainable by using said oligonucleotide in any of the assays capable of detecting nucleotide sequences and nucleotide sequence polymorphisms as described supra. Said signals include, e.g., fluorescent signals, (chemi) luminescent signals, radioactive signals, light signals, hybridization signals, mass spectrometric signals, spectrometric signals, chromatographic signals, electric signals, electronic signals, electrophoretic signals, real-time PCR signals, PCR signals, LCR signals, CFLP-assay signals and Invader-assay signals.

With "contacting an oligonucleotide with a (poly)nucleic acid" or vice versa is generally meant annealing of said oligonucleotide with said (poly)nucleic acid or hybridizing said oligonucleotide with said (poly)nucleic acid. "Contacting an oligonucleotide with a (poly)nucleic acid" does not exclude and can thus further comprise enzymatic modification of said oligonucleotide wherein said modification may occur at the extremities of said oligonucleotide and/or internally in the nucleotide sequence of said oligonucleotide. Examples of enzymatic modifications of oligonucleotides are given in, e.g., the assays capable of detecting nucleotide sequences and nucleotide sequence polymorphisms described herein.

In another embodiment of the invention said methods further comprise, where applicable, aligning and/or comparing the obtained nucleic acid sequence with a set of HBV nucleic acid sequences contained within a database.

With "database" is meant in the present context a collection of nucleic acid or amino acid sequences, more specifically of HBV nucleic acid or amino acid sequences. A database is to be understood to comprise at least one nucleic acid or at least one amino acid sequence. A database can be recorded on a variety of carriers. Such carriers include computer readable carriers.

Another aspect of the current invention relates to a diagnostic kit for detecting the presence of an HBV virus in a biological sample and/or for detecting resistance to an antiviral drug of an HBV virus present in a biological sample, said kit comprising at least a means for detecting the presence of an HBV polynucleic acid according to the invention.

A specific embodiment thereto includes said diagnostic kit comprising:
a. a means for infering, from the nucleic acid sequence of a target polynucleic acid suspected to comprise a serine-encoding codon 181 of the HBV reverse transcriptase domain optionally together with one or more codons from the group consisting of a methionine-encoding codon 180, an isoleucine-encoding codon 204 and an asparagine-encoding codon 236 of the HBV reverse transcriptase domain, the presence of said serine-encoding codon 181 of the HBV reverse transcriptase domain optionally together with one or more codons from the group consisting of a methionine-encoding codon 180, an isoleucine-encoding codon 204 and an asparagine-encoding codon 236 of the HBV reverse transcriptase domain, and, therefrom, the presence in said biological sample of said HBV and optionally,
b. a means for obtaining the nucleic acid sequence of the target polynucleic acid.

In a further specific embodiment, said diagnostic kit comprises an oligonucleotide capable of discriminating, in said HBV polynucleic acid, a codon 181 encoding a serine from a codon 181 encoding an alanine or valine and a further oligonucleotide capable of discriminating, in said HBV polynucleic acid, a codon 180 encoding a methionine from a codon 180 encoding a leucine.

In a further particular embodiment, said diagnostic kit comprises one oligonucleotide capable of discriminating, in said HBV polynucleic acid, a codon 181 encoding a serine from a codon 181 encoding an alanine or valine and also a codon 180 encoding a methionine from a codon 180 encoding a leucine.

In still a further specific embodiment, said diagnostic kit comprises an oligonucleotide capable of discriminating, in said HBV polynucleic acid, a codon 181 encoding a serine from a codon 181 encoding an alanine or valine and at least one, preferably at least two, more preferably at least three further oligonucleotide(s) chosen from the following group of oligonucleotides: an oligonucleotide capable of discriminating codon 236 encoding a threonine from a codon 236 encoding an asparagine; an oligonucleotide capable of discriminating, in said HBV polynucleic acid, a codon 204 encoding an isoleucine from a codon 204 encoding a methionine or valine or serine.

In yet another embodiment, said diagnostic kit additionally comprises a means for detecting the discriminatory signal obtained by contacting said HBV polynucleic acid with said oligonucleotide or oligonucleotides.

Furthermore embodied are said diagnostic kits wherein said oligonucleotide or oligonucleotides are attached or immobilized to a solid support.

Another specific embodiment thereto includes said diagnostic kits comprising:
a. a means for obtaining a target HBV polynucleic acid present in said biological sample and/or obtaining the nucleotide sequence thereof;
b. when appropriate, at least one oligonucleotide pair suitable for amplification of a target HBV polynucleic acid according to the invention;
c. when appropriate, a means for denaturing nucleic acids;
d. when appropriate, at least one oligonucleotide according to the invention;
e. when appropriate, an enzyme capable of modifying a double stranded or single stranded nucleic acid molecule;
f. when appropriate, a hybridization buffer, or components necessary for producing said buffer;
g. when appropriate, a wash solution, or components necessary for producing said solution;
h. when appropriate, a means for detecting partially or completely denatured polynucleic acids and/or a means for detecting hybrids formed in the preceding hybridization and/or a means for detecting enzymatic modifications of nucleic acids;
i. when appropriate, a means for attaching an oligonucleotide to a known location on a solid support;
j. a means for infering from the partially or completely denatured polynucleic acids and/or from the hybrids and/or from the enzymatic modifications, all detected in (h), and/or from the nucleotide sequence obtained in (a), the presence of said HBV virus in said biological sample.

With "a means for infering, from a nucleic acid sequence, the presence of codon Y (Y is number as indicated) encoding amino acid X (X is amino acid as indicated)" is meant any technique or method to (i) localize in said nucleic acid sequence said codon Y, (ii) to translate said codon Y into the amino acid encoded by codon Y, and (iii) to conclude from (ii) if the amino acid encoded by said codon Y is the same as or is different from said amino acid X. Said means can include methods wherein (i) to (iii) all are performed manually and/or computationally. Said means may include aligning and/or comparing an obtained nucleic acid sequence with a set of nucleic acid sequences contained within a database. Said means may furthermore include the result of (i) to (iii) being presented in the form of a report wherein said report can be in paper form, in electronic form or on a computer readable carrier or medium. Said means may furthermore include the searching of (nucleic acid and/or amino acid) sequence databases and/or the creation of (nucleic acid and/or amino acid) sequence alignments, the results of which may or may not be included in said report.

A further embodiment covers any of the above methods of the invention characterized further in that said methods are based on determining the nucleic acid sequence.

A further embodiment covers any of the above methods of the invention characterized further in that said methods are based on a hybridization assay.

A further embodiment covers any of the above methods of the invention characterized further in that said methods are based on a reverse hybridization assay.

A further embodiment covers any of the above diagnostic kits of the invention characterized further in that said diagnostic kits are based on determining the nucleic acid sequence.

A further embodiment covers any of the above diagnostic kits of the invention characterized further in that said diagnostic kits are based on a hybridization assay.

A further embodiment covers any of the above diagnostic kits of the invention characterized further in that said diagnostic kits are based on a reverse hybridization assay.

A further embodiment covers any of the above diagnostic kits of the invention characterized further in that said diagnostic kits are based on a line probe assay.

The invention further provides a method for detecting resistance to an antiviral drug of an HBV virus present in a biological sample, said method comprising the step of detecting the presence of an HBV DNA polymerase/reverse transcriptase protein or fragment according to the invention. Said detection may include the steps of determining the amino acid sequence of the HBV DNA polymerase/reverse transcriptase protein or from a part thereof obtained, e.g., after proteolytic digestion and separation of the resulting protein fragments via chromatographic and/or electrophoretic means. After electrophoresis, a protein fragment may be excised and eventually eluted from the gel before sequencing. Alternatively, the protein gel electrophoresis is combined with blotting whereby proteins are transfered to a membrane carrier (e.g. nitrocellulose, PVDF, nylon). The protein or protein fragment to be sequenced can in the latter case be excised from the membrane carrier. Alternatively, the HBV DNA polymerase/transcriptase protein according to the invention is detected using an antibody specifically recognizing the serine at position 181 of the HBV reverse transcriptase domain. In particular, said antibody should not recognize an alanine or valine at said position 181. In yet another alternative, the HBV DNA polymerase/reverse transcriptase according to the invention is detected phenotypically, i.e. said HBV DNA polymerase/transcriptase may display a unique pattern of antiviral drug sensitivity not shared with HBV DNA polymerase/reverse transcriptases comprising a codon 181 encoding an alanine or valine. Phenotypic detection of the HBV DNA polymerase/reverse transcriptase according to the invention thus includes e.g. the steps of determining the sensitivity of an activity of an HBV DNA polymerase/reverse transcriptase from an HBV virus present in a biological sample to a panel of antiviral drugs. Alternatively, the HBV DNA polymerase/reverse transcriptase from an HBV virus present in a biological sample and suspected to comprise a polynucleic acid according to the invention is produced in a recombinant system and the sensitivity to a panel of antiviral drugs is determined of an activity of the recombinantly expressed HBV DNA polymerase/reverse transcriptase.

It will be clear to the person skilled in the art that a vector system enabling HBV viral replication or enabling production of an HBV-encoded protein, or a functional part thereof, is suited for testing or assaying the effect of an antiviral drug on the HBV viral replication or function of the HBV-encoded protein (or part thereof), respectively. In particular, such assays can be performed with a mutant HBV polynucleic acid according to the present invention or with a mutant HBV DNA polymerase or mutant HBsAg protein according to the present invention. The results of such assays can be compared to results of similar assays performed with wild-type HBV polynucleic acids or wild-type HBV proteins, or functional parts thereof.

A person skilled in the art will appreciate that the HBV DNA polymerase/reverse transcriptase has multiple recognized biological/biochemical functions including primase activity, reverse transcriptase activity (RNA-dependent DNA polymerase activity), DNA polymerase activity (DNA-dependent DNA polymerase activity) and RNAse (RNAse H) activity and is furthermore involved in the interaction with the core antigen protein (HBcAg) and in the encapsidation of the viral DNA. Wild-type or mutant HBV DNA polymerase can be isolated from HBV particles present in a patient's serum or can be produced by e.g. a stably transformed hepatoma cell line. Alternatively, said HBV DNA polymerase is expressed and produced in a heterologous system (e.g. S. cerevisiae) or by using a baculovirus expression system, a mitochondrial translation system (e.g. as described in U.S. Pat. No. 6,100, 068) or in a cell-free system, e.g. a rabbit reticulocyte lysate coupled transcription-translation system (Li et al., 1999). Mutant HBV DNA polymerase DNA sequences can be produced by in vitro mutagenesis. Substantial purification of produced HBV DNA polymerase/reverse transcriptase can be achieved if e.g. a heterologous epitope (e.g. the FLAG epitope, cfr supra) is introduced in or fused to said HBV DNA polymerase/reverse transcriptase. Said epitope allows purification of the HBV DNA polymerase/reverse transcriptase e.g. on an affinity column containing immobilized anti-heterologous epitope antibodies (e.g. anti-FLAG M2 monoclonal antibodies). Alternatively, the recombinant HBV polymerase/reverse transcriptase is part of fusion protein, said fusion protein further comprising e.g. a histidine-tag, a carbohydrate-binding moiety (e.g. lectin, maltose binding protein) or β-galactosidase. Substantial purification of said fusion protein is achievable by e.g. metal-affinity chromatography (in case a histidine-tag is present), carbohydrate-affinity chromatography (in case a carbohydrate-binding moiety is present) or immuno-affinity chromatography using an antibody against the protein fused to the HBV DNA polymerase/reverse transcriptase, e.g. β-galactosidase. Optionally, said fusion protein is cleavable by a suitable protease (e.g. protease factor Xa) such that the HBV DNA polymerase/reverse transcriptase is obtainable separated from the other moiety of the fusion protein, e.g. by another round of purification as described supra. Alternatively, HBV viral particles are isolated from a biological sample by techniques such as affinity capture (e.g. using antibodies against the HBV viral surface antigen or using a protein receptor to said surface antigen or anti-idiotypic antibodies to said protein receptor, cfr. infra) or gradient centrifugation. HBV viral particles obtainable via these or other ways are further amenable to analysis e.g. of the HBV DNA polymerase/reverse transcriptase or of the HBV nucleic acids.

In yet another alternative, the multiprotein replicating core complex or intracellular replicating core are purified from infected liver cells and the obtained preparations comprising the HBV DNA polymerase/reverse transcriptase are used to assay the functions and activities of the HBV DNA polymerase/reverse transcriptase (Urban et al., 2000). Clearly, said purification of viral particles or of the replicating core complex can be applied to obtain said particles or core complex from cells infected with HBV variants comprising the mutation or mutations of the present invention.

Improved conditions for assaying viral reverse transcriptase activity have been described (Bird and Chang-Yeh in U.S. Pat. No. 5,817,457) and include acidic pH and elevated temperatures. Reaction conditions for assaying activity of RNAse H derived from the HBV DNA polymerase/reverse transcriptase have been described by e.g. Yoon et al. in U.S. Pat. No. 6,071,734. Assay conditions to determine primase-, polymerase-, and reverse transcriptase activity of in vitro produced HBV DNA polymerase/reverse transcriptase, or fragments thereof, have been described by Li et al. (Li et al., 1999). Assays to determine protein-protein interaction, e.g. interaction between the HBV DNA polymerase/reverse transcriptase and HBcAg, include two- and three-hybrid assays and real-time biomolecular interaction analysis (BIA). (Bartel et al., 1997 and U.S. Pat. No. 5,928,868).

Another additional aspect of the invention comprises an assay determining the effect of an antiviral drug on the function of a mutant HBsAg according to the present invention. A person skilled in the art will appreciate that the HBV HBsAg has multiple recognized biological/biochemical functions including functions in viral attachment/entry into the host cell (i.e. a role in infectivity of HBV), in viral particle assembly and in the secretion of viral particles. HBsAg is furthermore a target of the host's immune system and 'escape' mutants have been reported. The antibody against HBsAg, HBIg, is often used as a passive immunization means in patients that have undergone a liver transplant. Wild-type or mutant HBsAg can be obtained as described supra for HBV DNA polymerase. Alternatively, HBsAg is recovered by affinity interaction with antibodies against HBsAg or with an HBsAg receptor protein or with an anti-idiotypic antibody to said HBsAg receptor protein, said reported receptor proteins including monomeric and polymeric human albumin (Eibl et al. in U.S. Pat. No. 5,576,175 and Machida et al., 1984, respectively) and endonexinII/annexinV (Yap in European Patent No EP 0672136). HBV and HDV (hepatitis delta virus) viral particles may be isolated from a biological sample by techniques such as affinity capture e.g. using antibodies against the HBV viral surface antigen or using a receptor to the HBV viral surface antigen or anti-idiotypic antibodies thereto.

In an alternative aspect of the invention, activity of an HBV DNA polymerase/reverse transcriptase, including the mutant HBV DNA polymerase/reverse transcriptases of the invention, or the sensitivity thereof to antiviral compounds is assayed in host cells containing a conditional mutation in the endogenous DNA polymerase. As such, expression of the HBV DNA polymerase/reverse transcriptase can possibly rescue growth of said mutant host cells under restrictive conditions. Sensitivity of the HBV DNA polymerase/reverse transcriptase to antiviral compounds can be assayed by measuring the extent of growth of said mutant host cells under restrictive conditions and in the presence of an antiviral compound. Said growth is subsequently compared to growth of said host cells under restrictive conditions and in the absence of said antiviral compound.

In a further alternative aspect of the invention is included the use of mutant HBV particles, including HBV particles comprising a mutant DNA according to the present invention, to infect non-human animals which are useful as a model for human HBV infection or as a model for evaluating anti-HBV compounds, therapies and prohylaxes. Said model non-human animals have been described, e.g. by Reisner in U.S. Pat. Nos. 5,849,987 and 5,858,328. Many antiviral drugs against HBV (HBV antiviral drugs) are mentioned above.

A further aspect of the invention thus includes a method for screening for drugs active against an HBV virus comprising a polynucleic acid according to the invention or comprising an HBV DNA polymerase/reverse transcriptase according to the invention, said method comprising:
a. measuring replication of said HBV in the absence of said drug;
b. measuring replication of said HBV in the presence of said drug;
c. infering from (a) and (b) the inhibitory effect of said drug on replication of said HBV.

In a specific embodiment thereto, said method further comprises performing steps (a), (b) and (c) with a wild-type HBV virus and comparing the inhibitory effect of said drug on replication of said wild-type HBV virus with the inhibitory effect of said drug on replication of said HBV virus comprising a polynucleic acid according to the invention. In yet another further embodiment thereto are included said methods further comprising obtaining said HBV virus from a biological sample.

Yet another further embodiment of the invention includes a method for screening for drugs active against an HBV virus comprising a polynucleic acid according to the invention or comprising an HBV DNA polymerase/reverse transcriptase according to the invention, said method comprising:
a. measuring a DNA polymerase/reverse transcriptase activity of said HBV virus in the absence of said drug;
b. measuring the same DNA polymerase/reverse transcriptase activity as in (a) of said HBV virus in the presence of said drug;
c. infering from (a) and (ib) the inhibitory effect of said drug on said DNA polymerase/reverse transcriptase activity of said HBV virus.

In a specific embodiment thereto is included said method further comprising performing steps (a), (b) and (c) with a wild-type HBV virus and comparing the inhibitory effect of said drug on a DNA polymerase/reverse transcriptase activity of said wild-type HBV virus with the inhibitory effect of said drug on said DNA polymerase/reverse transcriptase activity of said HBV virus comprising a polynucleic acid according to the invention. In yet another further specific embodiment thereto are included said methods further comprising obtaining said HBV virus from a biological sample. With "a DNA polymerase/reverse transcriptase activity" is meant either one of the biological or biochemical activities of the HBV DNA polymerase/reverse transcriptase as mentioned supra.

The invention further embodies antibodies and anti-idiotypic antibodies against said isolated HBV variants and/or said isolated HBV small viral surface antigen, or said parts thereof, and/or said HBV middle and/or large viral antigens. In a specific embodiment thereto, said antibodies are monoclonal antibodies. In a further specific embodiment, said antibodies are humanized monoclonal antibodies.

Further embodied in the invention is the use of said antibodies in immunological methods for detecting said HBV variants and/or said HBV small viral surface antigen, or said parts thereof, and/or said HBV middle and/or large viral antigens in a biological sample. In a specific embodiment thereto, said antibodies are used in a method for diagnosing HBV infection. In a further embodiment, said antibodies are part of a diagnostic kit capable of detecting HBV infection.

In another embodiment of the invention is covered the use of a method of the invention or a diagnostic kit of the invention to follow progression of HBV infection.

A further embodiment covers the use of a method of the invention or a diagnostic kit of the invention to monitor the occurrence of resistance to an antiviral drug.

Another further embodiment covers the use of a method of the invention or a diagnostic kit of the invention to adapt a therapeutic regimen against HBV, infection due to the occurrence of resistance to an antiviral drug.

"Antibodies" include monoclonal, polyclonal, synthetic or heavy chain camel antibodies as well as fragments of antibodies such as Fab, Fv or scFv fragments. Monoclonal antibodies can be prepared by the techniques as described in e.g. Liddle et al. (Liddle et al., 1991) which comprise the fusion of mouse myeloma cells to spleen cells derived from immunized animals. Furthermore, antibodies or fragments thereof to a molecule or fragments thereof can be obtained by using methods as described in e.g. Harlow et al. (Harlow et al., 1988). In the case of antibodies directed against small peptides such as fragments of a protein of the invention, said peptides are generally coupled to a carrier protein before immunization of animals. Such protein carriers include keyhole limpet hemocyanin (KLH), bovine serum albumin (BSA), ovalbumin and Tetanus toxoid. The carrier protein enhances the immune response of the animal and provides epitopes for T-cell receptor binding sites. The term "antibodies" furthermore includes derivatives thereof such as labelled antibodies. Antibodies can generally be labeled radioactively, chemiluminescently, fluorescently, phosphorescently, with infrared dyes or with a surface-enhanced Raman label or plasmon resonant particle. Antibody labels include alkaline phosphatase, PKH2, PKH26, PKH67, fluorescein (FITC), Hoecst 33258, R-phycoerythrin (PE), rhodamine (TRITC), Quantum Red, Texas Red, Cy3, biotin, agarose, peroxidase and gold spheres. Tools in molecular biology relying on antibodies against a protein include protein gel blot analysis, screening of expression libraries allowing gene identification, protein quantitative methods including ELISA (enzyme-linked immunosorbent assay), RIA (radio-immuno-assay) and LIA (line immuno-assay), immunoaffinity purification of proteins, immunoprecipitation of proteins and immunolocalization of proteins.

According to the present invention, a novel mutation pattern, A181S+M204I, showing cross resistance to both lamivudine and adefovir was for the first time found. This mutation pattern was detected by direct sequencing of HBV DNA extracted from serum samples obtained both before and after adefovir treatment implying that this cross-resistant mutation pattern was primarily non-responsive to adefovir (FIG. 2).

Although lamivudine and adefovir have strong antiviral effects, development of mutants causing drug resistance presents an important problem in the treatment of chronic HBV infections. Moreover, existence of HBV mutation patterns with a cross resistance profile poses a major concern due to possibility of failure of combination therapies. Adefovir has been generally regarded as a good treatment option in the treatment of patients who failed lamivudine therapy because of drug resistant HBV.

However according to the present invention the use of adefovir dipivoxil in combination with lamivudine during the therapy neither suppressed HBV replication nor decreased serum ALT levels (see especially FIG. 1), which suggests that the A181S and A181S+M204I variants demonstrate cross-resistance in vivo for both adefovir and lamivudine. A181S mutation was detected in all available serum samples starting from month 28 of commencing antiviral treatment, i.e. before virological and biochemical breakthrough. The M204I mutation, on the other hand, was not detected in the first available serum sample at month 28 but emerged 3 months later at month 31, i.e. at the time of breakthrough.

In vitro findings confirmed that this HBV mutant is resistant to adefovir even when treated with high concentrations, such as 10 µM of adefovir dipivoxil (see especially table 2). Similarly, this variant was found to be resistant to lamivudine in vitro at all concentrations of lamivudine tested, which is consistent with the previously reported resistance profile of mutations in the YMDD motif (Bozdayi et al., 2003; Seta et al., 2000). Taken together, the above data indicate that the A181S+M204I variant exhibits cross-resistance to adefovir and lamivudine both in vivo and in vitro.

It unfortunately seems that the use of combination therapy is not able to prevent, but delay the occurrence of novel drug resistant mutants. Anyhow, the best option to combat HBV infection in today's clinical practice is still to combine antiviral drugs with different resistance profile.

The following examples only serve to illustrate the present invention further. These examples are in no way intended to limit the scope of the present invention.

EXAMPLES

Example 1

A New Mutation Pattern Developed in a HBV Strain During 3TC-Treatment Shows Cross-Resistance to Adefovir Dipivoxil Treatment Case Study In work leading to the present invention, the inventors have identified a patient that was chronically infected with HBV. The patient was a 43-year old Caucasian male indicated with patient AA with known HBV infection since 1990, diagnosed during a routine check-up. A liver biopsy in 1999 revealed chronic active hepatitis (CAH) with a histological activity index of six according to Knodell et al. The patient was HbeAg positive, anti-Hbe negative as well as positive for HBV DNA. HBV DNA levels were measured by using a commercial liquid-hybridization assay (Digene, Maryland, US), with the lower limit of detection of this assay being 5 pg/mL of viral DNA.

As represented in FIG. 1, IFN therapy, 9 MU/TIW (million units/three times in one week), was given for 9 months (in 1999). The patient did not show an ALT decrease or virological response (HBV DNA level was 396 pg/ml at the end of IFN treatment). As the viral load failed to decrease within this period, the patient discontinued IFN therapy after nine months of treatment and started lamivudine (LAM) treatment, 100 mg/day. During LAM treatment, there was normalization of the ALT level and replication inhibition of HBV. After 19 months of LAM treatment, clinical breakthrough occurred, characterized by an ALT flare and detection of HBV DNA by a hybridisation assay. Lamuvidine was continued after the development of clinical breakthrough. IFN (9 MU/TIW) was added again for 6 months, when a seroconversion sign (appearance of anti-hbe and dissappearance of HbeAg). However, the combination therapy did not lead to normalization of liver enzymes and HBV DNA levels remained high during this period. IFN was stopped 6 months after its addition and after a sustained seroconversion occurred. Hepsera™ (Adefovir dipovoxil) 10 mg/day was added to lamivudine monotherapy at 44$^{th}$ month of initial antiviral therapy and 3 months after stopping IFN. Hepsera™ was used for a longer period of 14 months; neither inhibition of HBV replication nor ALT normalization occurred.

Effect of Antiviral Therapy

LAM treatment was initially successful. There was normalisation of the level of ALT and replication inhibition of HBV. At month 19 of LAM treatment clinical breakthrough occurred. The addition of Hepsera™ to Lamivudine monotherapy did not lead to inhibition of HBV replication and ALT normalisation. Blood counts and liver-function tests (alanine and aspartate aminotransferases) were done according to routine biochemical procedures (Olympus AU 2700 autoanalyzer, Japan).

Isolation and Sequencing of HBV DNA

Serum was withdrawn from the patient at different intervals (months 28, 31, 42, 51, 57, 61) from the start of antiviral treatment. HBV-DNA was each time isolated from serum of the patient with the use of a Qiamp DNA mini kit (Qiagen, Hilden, Germany) according to the manufacturer's instruction. The HBV DNA-polymerase gene was amplified by PCR. Briefly, 5 microliters of the DNA samples were made up to 50 µL with a PCR mixture containing 10 mM Tris HCl, pH: 8.3, 50 mM KCl, 1.5 mM MgCl$_2$, 2 mM dNTP, 25 pmol/µL of sense and anti-sense primers and 2.5 Units of Taq DNA polymerase (RocheDiagnostic, Penzberg, Germany). To amplify the HBV polymerase gene, the thermalcycler (GeneAmp PCR system 9700, PE, Applied Biosystems, Foster City, Calif.; US) was programmed for 35 cycles of denaturating at 94° C. for 1 min, annealing at 45° C. for 1 min, polymerization for 2 min was performed. The conditions for the second round PCR were the same as those for the first round using 5 µL of the sample from the first round PCR. Additionally, two sets of nested primer pairs were used to augment the HBV polymerase gene. Outer primers were 5'CAC CTG CAG CCT CAT TTT GTG GGT CAC CAT A3' (SEQ ID NO: 21) and 5'CAT AAG CTT CAC AAT TCG TTG ACA TAC TTT CCA AT3' (SEQ ID NO: 22), and inner primers were 5'GTG CTG CAG TTT GTG GGT CAC CAT ATT CTT G3' (SEQ ID NO: 23) and 5'GAC AAG CTT TTG ACA TAC TTT CCA ATC AAT AG3' (SEQ ID NO:24) (Ogata et al., 1999; in each sequence nucleotides 4 to 9 denote enzyme recognition sites for Pst I and Hind III). Amplified products were run on 2% agarose gel stained with ethidium bromide. Sequencing was carried out directly on the amplified PCR products. The PCR products were purified by commercially available PCR cleaning kit (Nucleospin Extract kit, Macherey-Nagel, Düren, Germany), according to the manufacturers instruction. Direct sequencing of the PCR products was performed using primers used for PCR and the big dye terminator cycle sequencing kit (Applied Biosystems, Foster City, Calif., US). For each sequencing reaction, not only sense inner primer, but also antisense inner primer was used to confirm the sequences. The reaction products were run on the ABI 310 (PE, Applied Biosystems, Foster City, Calif., US US) automated sequencer. The results are shown in FIG. 2.

PCR products obtained from serum withdrawn at month 42 (June 2002) were subsequently also cloned into a TA vector (Topo TA cloning kit, Invitrogen, Carlsbad, Calif., US) according to routine cloning procedures. Out of nine clones, seven were sequenced. The results are shown in FIG. 3. The mutation pattern D205G found in clone 4 has to be confirmed again.

Nucleotide Changes

The sequence results of FIG. 2 show that in all samples taken from the patient at different intervals, nucleotide mutations that result in amino acid substitution rtA181S and rtM204I were present. Thus, the rtM204I mutation along with the rtA181S mutation was detected in all samples obtained since the development of lamivudine resistance. For rtA181, two mutation patterns were shown so far. However, rtA181S is a new pattern.

Sequence information obtained from the cloned PCR product amplified from serum obtained at month 42 is shown in FIG. 3. The sequence results showed that two out of seven clones comprised nucleotide mutations that result in amino acid substitutions rtL180M and rtM204S. These mutations have been associated with LAM resistance. The other five out of seven clones comprised nucleotide mutations that result in amino acid substitutions rtA181S and rtM204I. One clone was found to comprise nucleotide mutations wich resulted in amino acid substitutions rtA181S, rtM204I and rtD205G.

RtA181S is a mutation pattern commonly found among the sequenced results. Present results (no inhibition of HBV replication and fluctuation of ALT levels at the end of the 14$^{th}$ month) allow us to conclude that the mutation pattern rtA181S arising under lamivudine treatment shows a cross resistance to Adefovir Dipivoxil. More in particular, mutation pattern rtA181S in combination with rtM204I shows a cross resistance to Adefovir Dipivoxil.

It is concluded that the drug resistant strain with a new mutation pattern selected under lamivudine treatment is also cross resistant to adefovir treatment.

Example 2

In-Vitro Confirmation of the Drug-Resistance of the Newly Mutated HBV Strain

Isolation of HBV DNA From Serum Samples and Amplifacation of Full-Length HBV Genomes DNA was extracted from 200 μl serum samples using High Pure Viral Nucleic Acid kit (Roche, Ind., USA) according to the manufacturer's instructions. The full-length HBV DNA genome was amplified as previously reported by Gunther et al., 1995 using a PCR system containing 50 mM KCl, 1.5 mM $MgCl_2$, 0.35 mM Tris-HCl (pH 8.3), 200 μM dNTP, 5 U of Taq DNA polymerase and 0.3 μM of each of the following primers: [P1, 5'-CCGGA AAGCTT GAGCTC TTCTTTTT CACCTC TGCCT AATCA-3' (nucleotide 1821-1841; SEQ ID NO 25); P2, 5'-CCGGA AAGCTT GAGCTC TTCAAAAA GTTGC ATGGTG CTGG-3' (nucleotide 1823-1806; SEQ ID NO 26)] and 2 μl of extracted DNA in a total volume of 50 μl PCR reaction was run for 40 cycles with denaturation at 94° C. for 40 s, annealing at 60° C. for 1.5 min and elongation at 68° C. for 3 min, with an addition of 2 min after each of 10 cycles in "Eppendorf Mastercycler Personal".

Direct Sequencing of Full-Length HBV Genomes

Direct DNA sequencing was performed for both the amplified products directly extracted from serum samples and for the constructs of TA cloning using "Big Dye Terminator v3.1 Cycle Sequencing Kit" (Applied Biosystems, Fostercity, USA) according to manufacturer's instructions in "ABI PRISM 310 Genetic Analyzer" (Perkin Elmer, Foster City, USA). PCR products were purified using a "Qiaquick PCR purification kit" (Quiagen, Hilden, Germany) prior to sequencing. The primers used in the direct sequencing are listed in table 1.

TABLE 1

Primers used in the direct sequencing of full-length HBV DNA

| Primers | Binding regions (bp) | DNA sequence | SEQ ID NO |
|---|---|---|---|
| HBV (676-699) | 676-699 | 5' TTTACTAGTGCCATTTGTTCAGTG 3'* | 27 |
| HBV (66-90): | 66-90 | 5' GCTCCAGTTCAGGAACAGTAAACCC 3'* | 28 |
| HBV (2796-2826) | 2796-2826 | 5' CACCTGCAGCCTCATTTTGTGGGTCACCATA 3'* | 29 |
| HBV (2357-2380) | 2357-2380 | 5' GGCAGGTCCCCTAGAAGAAGAACT 3'* | 30 |
| HBV (2432-2408) | 2432-2408 | 5' ATTGAGATCTTCTGCGACGCGGCGA 3'* | 31 |
| HBVCP11 | 1694-1717 | 5' GACCTTGAGGCATATTTCAAAGAC 3'** | 32 |
| HBVCP13 | 2069-2047 | 5' CTGAGTGCTGTATGGTGAGGTGA 3'** | 33 |

*Gunther et al, 1995
**Bozdayi et al, 2001

TA Cloning of Full-Length HBV Genomes and Characterization of HBV Genomes by PCR and Sequencing The amplified full-length HBV genomes were cloned into a TA vector using Topo-XL PCR Cloning" (Invitrogen, Calif., USA) according to manufacturer's instructions. The constructs were then sequenced. Full-length HBV genome within the clone harboring the A181S+M204I mutation pattern was further amplified as described earlier. Same procedure was also applied for the clone bearing wild type HBV genome.

Preparation of HBV DNA for Direct Transfection

The amplicons were gel-purified using "QIAquick Gel Extraction kit" (QUIAGEN, Basel, Switzerland) according to the instructions provided with the kit and pooled. Subsequent digestion with 5U of sapI restriction endonuclease per μg of DNA released linear HBV genomes with sapI sticky ends devoid of vector and heterologous primer sequences.

Transfection and In Vitro Replication of HBV DNA for Antiviral Susceptibility Testing The in vitro replication ability of full-genome HBV DNA was measured by transient transfection into Huh7 cell lines. The 24-well plates wereμg GFP containing plasmid, which was used to determine the transfection efficiency using Fugene transfection reagent (Roche Diagnostics). Eight hours after transfection, cells were fed with fresh medium alone to test the replication efficiency or with medium containing 0.1 μM, 1 μM, 10 μM lamivudine or adefovir alone to test the antiviral susceptibilities. The supernatant of the cells fed with only fresh medium was collected every day during 5 days and the supernatant of the cells fed with antiviral containing medium was collected at the end of the $5^{th}$ day. Viral DNA extraction was performed using "QIAamp DNA Mini Kit" (QUIAGEN, Basel, Switzerland) according to manufacturer's instructions. The HBV DNA was measured with Real-Time PCR method using "Fast Start DNA hybridization kit" (Roche Diagnostics, GmbH, Indianapolis, ABD) according to the protocol used in Bozkaya et al., 2005.

HBV Replication in Transiently Transfected HUH7 Cell Lines

The replication ability of full-length HBV genomes was analysed in vitro. Real Time PCR analysis performed with the HBV replicates extracted from the supernatant of each day demonstrated that measured total HBV production in the cell culture reached to a logarithmic copy number of almost 5 at the end of $5^{th}$ day (FIG. 4). This result confirms that transfected HBV DNA is replication competent in vitro.

Analysis of Effects of Lamivudine and Adefovir on Wild Type and Mutant (A181S+M204I) Viruses Drug susceptibility of A181S+M204I mutation pattern was tested against wild type HBV using increasing concentrations of lamivudine (0.1 μM, 1 μM, 10 μM ) or adefovir (0.1 μM, 1 μM and 10 μM) by performing 3 independent experiments, see table 2.

TABLE 2

HBV production in vitro measued by Real-time PCR analysis

| | HBV replication in transiently transfected Huh7 cell lines (Mean log HBV copy number ± standard deviation) | |
|---|---|---|
| Antivirals | Wild type | A181S + M204I |
| No drug | 4.56 ± 0.73 | 4.75 ± 0.88 |
| 3TC (0.1 μM) | 4.1 ± 0.8 | 4.82 ± 0.19 |
| 3TC (1 μM) | 2.32 ± 1.62 | 4.44 ± 1.03 |
| 3TC (10 μM) | n.d. | 4.68 ± 0.82 |
| Adefovir (0.1 μM) | 1.15 ± 1.62 | 4.71 ± 0.42 |
| Adefovir (1 μM) | 0.32 ± 0.58 | 4.48 ± 0.43 |
| Adefovir (10 μM) | n.d. | 4.12 ± 0.98 | n.d. not detectable

HBV genome carrying A181S+M204I mutation pattern was found to be resistant to both lamivudine and adefovir even in the high concentrations of antivirals. While there was no detectable HBV DNA of wild type HBV in the samples treated with 10 μM of lamivudine and adefovir, log copy numbers of 4.68+0.82 and 4.12+0.98 were measured for those of mutant HBV (table 2), respectively.

Example 3

Confirmation of the Mutation Pattern in the HBV Strain in Another Patient

A 33 years old man is a patient with HBsAg (+) and Anti-HBe (+). He was found to be positive for HBsAg in 1998. He was treated with IFN 9MIU thrice weekly in 2003 for 12 month (ALT: 242 IU/L, AST: 155 IU/L and HBV DNA: 3260 pg/mL by liquid hybridization assay of Digene, US, before the start of IFN treatment. Due to incomplete response, lamivudine was started in 2004 (Zeffix, 100 mg/day). Following the lamivudine treatment, ALT normalisation was obtained and HBV DNA levels were less than 5 pg/mL. However, at the 20 th month of lam treatment, a clinical breakhthrough characterized by ALT flare and restoration of HBV replication (ALT: 199 IU/mL, AST: 145 IU/mL and HBV DNA: 6540 pg/mL) occured. The 2 serum samples obtained after start of lam treatment and clinical breakthrough were extracted and complete genome of HBV DNA was amplified according to the method by Gunther et al., 1995 in both extracted materials. The PCR products were then cloned into TA vectors and 8 clones from each were sequenced by cycle sequencing method in 310 ABI (US). The sequences of the 4 clones belonging to the just after the start of lamivudine treatment were representing wild type sequences. However, the sequences of all the 8 clones obtained after the clinical breakthrough displayed A181S+M204I pattern (GCT to TCT in 181st codon and ATT to ATC in 204th codon).

REFERENCES

Angus P. et al. Resistance to adefovir dipivoxil therapy associated with the selection of a novel mutation in the HBV polymerase. *Gastroenterology* (2003) 125(2): 292-297.

Arguello, J. R., Little, A. M., Pay, A. L., Gallardo, D., Rojas, I., Marsh, S. G., Goldman, J. M. & Madrigal, J. A. (1998) Nat Genet 18, 192-194

Bartel, P. L. & Fields, S. (1997) The yeast two-hybrid system. Oxford University Press, Beaucage, S. L. (2001) Curr Med Chem 8, 1213-1244

Benhamou Y. et al. Antiretroviral therapy and HIV/hepatitis B virus coinfection. *Clin. Infect. Dis.* (2004) 38 Suppl 2: S98-103.

Benhamou Y. et al. Safety and efficacy of adefovir dipivoxil in patients co-infected with HIV-1 and lamivudine-resistant hepatitis B virus: an open-label pilot study. *Lancet* (2001) 358: 718-723.

Benhamou Y. et al. Tenofovir disoproxil fumarate in patients with HIV and lamivudine-resistant hepatitis B virus. *N. Engl. J. Med.* (2003) 348(2): 177-178.

Bozdayi, A. M., Bozkaya, H., Türkyilmaz, A. R., Sarioglu, M., Cetinkaya, H., Karayalcin, S., Yurdaydin, C., Uzunalimoglu, Ö. (2001): Nucleotide divergences in the core promoter and precore region of genotype D hepatitis B virus in patients with persistently elevated or normal ALT levels. J Clin Virol. 21(1): 91-101

Bozdayi A m, Uzunalimoglu O, Turkyilmaz A r, Aslan N, Sezgin O, Sahin T, Bozdayi G, Cinar K, Pai S b, Pai R, Bozkaya H, Karayalcin S, Yurdaydin C, Schinazi R f. (2003). YSDD: a novel mutation in HBV DNA polymerase confers clinical resistance to lamivudine. J. Viral Hepat., 10: 256-65.

Bozkaya H, Yurdaydin C, Idilman R, Tuzun A, Cinar K, Erkan O, Bozdayi A M, Erden E, Uzun Y, Cetinkaya H & Uzunalimoglu O. (2005) Lamivudine treatment in HBeAg-negative chronic hepatitis B patients with low level viraemia. Antivir Ther. 10(2): 319-25

Day, I. N., Spanakis, E., Palamand, D., Weavind, G. P. & O'Dell, S. D. (1998) Trends Biotechnol. 16, 287-290

De Clercq, E. (1999) Int. J Antimicrob Agents 12, 81-95

Delaney, W. E., Miller, T. G. & Isom, H. C. (1999) Antimicrob Agents Chemother 43, 2017-2026

Delaney W, Yang H, Westland C, Das K, Arnold E, Miller M. (2002). Functional analysis of rtV173L, an HBV polymerase mutation frequently observed in lamivudine-resistant chronic hepatitis B patients. Hepatology, 36: 373A Delwart, E. L., Sheppard, H. W., Walker, B. D., Goudsmit, J. & Mullins, J.1. (1994) J Virol 68, 6672-6683

Delwart, E. L., Shpaer, E. G., Louwagie, J., McCutchan, F. E., Grez, M., Rubsamen-Waigmann, H. & Mullins, J. I. (1993) Science 262, 1257-1261

Dore G. J. et al. Efficacy of tenofovir disoproxil fumarate in antiretroviral therapy-naive and experienced patients coinfected with HIV-1 and hepatitis B virus. *J. Infect. Dis.* (2004) 189 (7): 1185-1192.

Drmanac, R., Drmanac, S., Strezoska, Z., Paunesku, T., Labat, I., Zeremski, M., Snoddy, J., Funkhouser, W. K., Koop, B. & Hood, L. (1993) Science 260, 1649-1652

Fu, L. & Cheng, Y. C. (2000) Antimicrob Agents Chemother 44, 3402-3407

Griffin, T. J. & Smith, L. M. (2000) Trends Biotechnol. 18, 77-84

Gunther S, Li B C, Miska S, Kruger D H, Meisel H & Will H. (1995) A novel method for efficient amplification of whole hepatitis B virus genomes permits rapid functional analysis and reveals deletion mutants in immunosuppressed Patients. J Virol 69, 5437-5444.

Harlow, E. & Lane, D. (1988) Antibodies: A Laboratory Manual. Cold Spring Harbor Laboratory Press Huber, C. G., Premstaller, A., Xiao, W., Oberacher, H., Bonn, G. K. & Oefner, P. J. (2001) J Biochem Biophys Methods 47, 5-19

Jarvis, B. & Faulds, D. (1999) Drugs 58, 101-141

Knodell, R. G., Ishak, K. G., Black, W. C., Chen, T. S., Craig, R., Kaplowitz, N., Kiernan, T. W. & Wollman, J. (1981) Hepatology 1, 431-435

Korkko, J., Annunen, S., Pihlajamaa, T., Prockop, D. J. & Ala-Kokko, L. (1998) Proc Natl Acad Sci U S A 95, 1681-1685

Kosovsky, M. J., Khaoustov, V. I., Rushton, M. & Yoffe, B. (2000) Biochim Biophys Acta 1490, 63-73

Kristensen, V. N., Kelefiotis, D., Kristensen, T. & Borresen-Dale, A. L. (2001) Biotechniques 30, 318-22, 324, 326

Li, Z. & Tyrrell, D. L. (1999) Biochem Cell Biol 77, 119-126

Liddle, J. E. & Cryer, A. (1991) A Practical Guide to Monoclonal Antibodies. Wiley, New York Lok, A. S. (1994) J Viral. Hepat. 1, 105-124

Lu, X., Block, T. M. & Gerlich, W. H. (1996) J Virol 70, 2277-2285

Lu, X., Hazboun, T. & Block, T. (2001) Virus Res 73, 27-40

Luscombe, C. A. & Locarnini, S. (1996) Viral hepatitis reviews 2, 1-35

Machida, A., Kishimoto, S., Ohnuma, H., Baba, K., Ito, Y., Miyamoto, H., Funatsu, G., Oda, K., Usuda, S. & Togami, S. (1984) Gastroenterology 86, 910-918

Maxam, A. M. & Gilbert, W. (1977) Proc Natl Acad Sci U S A 74, 560-564

Meller, A., Nivon, L., Brandin, E., Golovchenko, J. & Branton, D. (2000) Proc Natl Acad Sci USA 97, 1079-1084

Narayanaswami, G. & Taylor, P. D. (2001) Genet Test. 5, 9-16

Nielsen, P. E. (2001) Curr Med Chem 8, 545-550

Ogata N., Fujii K., Takigawa S., Nomoto M., Ichida T. & Asakura H. (1999) J. Med. Virol. 59, 270-276.

Ono, S. K., Kato, N., Shiratori, Y., Kato, J., Goto, T., Schinazi, R. F., Carrilho, F. J. & Omata, M. (2001) J Clin Invest 107, 449-455

Orum, H. & Wengel, J. (2001) Curr Opin. Mol. Ther. 3, 239-243

Paran, N., Geiger, B. & Shaul, Y. (2001) EMBO J 20, 4443-4453

Perrillo R. et al. Adefovir dipivoxil added to ongoing lamivudine in chronic hepatitis B with YMDD mutant hepatitis B virus. *Gastroenterology* (2004) 126(1): 81-90.

Peters M. G. et al. Adefovir dipivoxil alone or in combination with lamivudine in patients with lamivudine-resistant chronic hepatitis B. *Gastroenterology* (2004) 126(1): 91-101.

Resch, W., Parkin, N., Stuelke, E. L., Watkins, T. & Swanstrom, R. (2001) Proc Natl Acad Sci USA 98, 176-181

Ruano, G. & Kidd, K. K. (1991) Proc Natl Acad Sci U S A 88, 2815-2819

Saiki, R. K., Walsh, P. S., Levenson, C. H. & Erlich, H. A. (1989) Proc Natl Acad Sci U S A 86, 6230-6234

Sanger, F., Nicklen, S. & Coulson, A. R. (1977) Proc Natl Acad Sci U S A 74, 5463-5467

Schinazi, R. (1997) in Viral hepatitis and liver disease (Rizzetto, M., Purcell, R., Gerin, J. & Verme, G., eds.), Impact of nucleosides on hepatitis virus. pp. 736-742, Minerva Medica, Torino Seta, T., O. Yokosuka, F. Imazeki, M. Tagawa, and H. Saisho (2000). Emergence of YMDD motif mutants of hepatitis B virus during lamivudine treatment of immunocompetent type B hepatitis patients J. Med. Virol. 60: 8-16.

Stuyver, L., De Gendt, S., Van Geyt, C., Zoulim, F., Fried, M., Schinazi, R. F. & Rossau, R. (2000) J Gen. Virol 81 Pt 1, 67-74

Stuyver, L., Wyseur, A., Rombout, A., Louwagie, J., Scarcez, T., Verhofstede, C., Rimland, D., Schinazi, R. F. & Rossau, R. (1997) Antimicrob Agents Chemother 41, 284-291

Stuyver, L., Wyseur, A., van Arnhem, W., Hernandez, F. & Maertens, G. (1996) J Clin Microbiol 34, 2259-2266

Stuyver, L. J., Locamini, S. A., Lok, A., Richman, D. D., Carman, W. F., Dienstag, J. L. & Schinazi, R. F. (2001) Hepatology 33, 751-757

Summers J., Mason W. *Cell* (1982) 29: 403-415.

Urban, S. & Tyrrell, D. L. (2000) Antiviral Res 45, 185-197

Wahlestedt, C., Salmi, P., Good, L., Kela, J., Johnsson, T., Hokfelt, T., Broberger, C., Porreca, F., Lai, J., Ren, K., Ossipov, M., Koshkin, A., Jakobsen, N., Skouv, J., Oerum, H., Jacobsen, M. H. & Wengel, J. (2000) Proc Natl Acad Sci U S A 97, 5633-5638

Westland C E et al. Week 48 resistance surveillance in two phase 3 clinical studies of adefovir dipivoxil for chronic hepatitis B. *Hepatology* (2003) 38(1): 96-103.

Xiao, W. & Oefner, P. J. (2001) Hum Mutat 17, 439-474

Xiong, X., C. Flores, H. Yang, J. J. Toole, and C. S. Gibbs. (1998). Mutations in hepatitis B DNA polymerase associated with resistance to lamivudine do not confer resistance to adefovir in vitro Hepatology 28: 1669-1673.

Yager, T. D., Baron, L., Batra, R., Bouevitch, A., Chan, D., Chan, K., Darasch, S., Gilchrist, R., Izmailov, A., Lacroix, J. M., Marchelleta, K., Renfrew, J., Rushlow, D., Steinbach, E., Ton, C., Waterhouse, P., Zaleski, H., Dunn, J. M. & Stevens, J. (1999) Electrophoresis 20, 1280-1300

Yang H. et al. Complete Genotypic and Phenotypic Analyses of HBV Mutations Identified in HBeAg-negative Chronic Hepatitis B Patients Receiving 96 Weeks of Adefovir Dipivoxil (ADV). *Hepatology* (2003) 38: 705A., C. T., Chien, R. N., Chu, C. M. & Liaw, Y. F. (2000) Hepatology 31, 1318-1326

The invention claimed is:

1. A method for detecting the presence of an HBV variant in a biological sample, said HBV variant comprising at least one nucleotide mutation in the DNA polymerase gene at codon 181 which results in an alanine to serine amino acid substitution rtA181S, said method comprising the step of detecting the presence of a HBV polynucleic acid in a biological sample, said HBV polynucleic acid comprising a nucleotide mutation that results in an amino acid substitution rtA181S of the DNA polymerase gene in the HBV variant, or a fragment of said HBV polynucleic acid comprising said nucleotide mutation.

2. A method according to claim 1 comprising:
  a) obtaining a target HBV polynucleic acid from said biological sample wherein said target HBV polynucleic acid is suspected to comprise a serine-encoding codon 181 of the HBV reverse transcriptase domain, and optionally one or more of the codons chosen from the group consisting of a methionine-encoding codon 180, an isoleucine-encoding codon 204 or a valine-encoding codon 204 or a serine-encoding codon 204, and a threonine encoding codon 236 of the HBV reverse transcriptase domain of an HBV virus;
  b) obtaining the nucleic acid sequence of the target HBV polynucleic acid of (a);
  c) infering, from the nucleic acid sequence obtained in (b), the presence of said serine-encoding codon 181 of the HBV reverse transcriptase domain, and optionally one or more codons chosen from the group mentioned in (a) and, therefrom, the presence of said HBV virus in said biological sample.

3. A method according to claim 2 comprising:
  a) obtaining a target HBV polynucleic acid present in said biological sample and/or obtaining the nucleotide sequence thereof;
  b) optionally, partially or completely denaturating, or enzymatically modifying the polynucleic acids obtained in step (a);
  c) optionally, renaturating the denatured polynucleic acids obtained in step (b),
  optionally in the presence of at least one oligonucleotide capable of discriminating, in an HBV polynucleic acid or a fragment thereof a serine-encoding codon 181 in the HBV reverse transcriptase domain from a codon 181 encoding an alanine or a valine in the HBV reverse transcriptase domain, and, optionally, including the step of enzymatically modifying, including extending, said oligonucleotide;
d) optionally, detection of the partially or completely denatured HBV polynucleic acids obtained in step (b), and/or of the hybrids formed in step (c), and/or of the enzymatic modifications obtained in step (b) and/or (c);
e) infering from one or more of the data of the following groups: the partially or completely denatured polynucleic acids, the hybrids, the enzymatic modifications, all detected in step (d), and from the nucleotide sequence obtained in (a), the presence of said HBV in said biological sample.

4. The method for detecting the presence of an HBV variant according to claim 1 comprising:
a) obtaining a target HBV polynucleic acid from said biological sample wherein said target HBV polynucleic acid is suspected to comprise a serine-encoding codon 181 of the HBV reverse transcriptase domain, optionally together with one or more of the codons chosen from the group consisting of a methionine-encoding codon 180, an isoleucine encoding codon 204 or a valine-encoding codon 204 or a serine-encoding codon 204, and a threonine encoding codon 236 of the HBV reverse transcriptase domain of an HBV;
b) contacting the target HBV polynucleic acid of (a) with an oligonucleotide capable of discriminating a codon 181 encoding a serine from a codon 181 encoding an alanine or valine, and optionally also capable of discriminating one or more codons chosen from the group consisting of a codon 180 encoding a leucine from a codon 180 encoding a methionine, a codon 204 encoding an isoleucine from a codon 204 encoding a methionine, valine or serine, and a codon 236 encoding an asparagine from a codon 236 encoding a threonine
c) infering, from the discriminatory signal obtained in (b), the presence of said serine-encoding codon 181 of the HBV reverse transcriptase, optionally together with said methionine-encoding codon 180 or said isoleucine-encoding codon 204 or said asparagine-encoding codon 236 of the HBV reverse transcriptase domain and, therefrom, the presence of said HBV in said biological sample.

5. A method for detecting the resistance of an HBV virus present in a biological sample to an antiviral drug, said HBV variant comprising at least one nucleotide mutation in the DNA polymerase gene at codon 181 which results in an alanine to serine amino acid substitution rtA181S, said method comprising the step of detecting the presence of a HBV polynucleic acid comprising a nucleotide mutation that results in an amino acid substitution rtA181S of the DNA polymerase gene in the HBV variant, or a fragment of said HBV polynucleic acid comprising said nucleotide mutation, wherein the presence of said HBV polynucleic acid indicates resistance of an HBV virus present in said biological sample to an antiviral drug.

6. A method according to claim 5 comprising:
a) obtaining a target HBV polynucleic acid from said biological sample wherein said target HBV polynucleic acid is suspected to comprise a serine-encoding codon 181 of the HBV reverse transcriptase domain, and optionally one or more of the codons chosen from the group consisting of a methionine-encoding codon 180, an isoleucine-encoding codon 204 or a valine-encoding codon 204 or a serine-encoding codon 204, and a threonine encoding codon 236 of the HBV reverse transcriptase domain of an HBV virus;
b) obtaining the nucleic acid sequence of the target HBV polynucleic acid of (a);
c) infering, from the nucleic acid sequence obtained in (b), the presence of said serine-encoding codon 181 of the HBV reverse transcriptase domain, and optionally one or more codons chosen from the group mentioned in (a) and, therefrom said resistance of an HBV virus present in said biological sample to an antiviral drug.

7. A method according to claim 6 comprising:
a) obtaining a target HBV polynucleic acid present in said biological sample and/or obtaining the nucleotide sequence thereof;
b) optionally, partially or completely denaturating, or enzymatically modifying the polynucleic acids obtained in step (a);
c) optionally, renaturating the denatured polynucleic acids obtained in step (b),
optionally in the presence of at least one oligonucleotide capable of discriminating, in an HBV polynucleic acid or a fragment thereof a serine-encoding codon 181 in the HBV reverse transcriptase domain from a codon 181 encoding an alanine or a valine in the HBV reverse transcriptase domain, and, optionally, including the step of enzymatically modifying, including extending, said oligonucleotide;
d) optionally, detection of the partially or completely denatured HBV polynucleic acids obtained in step (b), and/or of the hybrids formed in step (c), and/or of the enzymatic modifications obtained in step (b) and/or (c);
e) infering from one or more of the data of the following groups: the partially or completely denatured polynucleic acids, the hybrids, the enzymatic modifications, all detected in step (d), and from the nucleotide sequence obtained in (a), the resistance of an HBV virus present in said biological sample to an antiviral drug.

8. The method according to claim 5 comprising:
a) obtaining a target HBV polynucleic acid from said biological sample wherein said target HBV polynucleic acid is suspected to comprise a serine-encoding codon 181 of the HBV reverse transcriptase domain, optionally together with one or more of the codons chosen from the group consisting of a methionine-encoding codon 180, an isoleucine encoding codon 204 or a valine-encoding codon 204 or a serine-encoding codon 204, and a threonine encoding codon 236 of the HBV reverse transcriptase domain of an HBV;
b) contacting the target HBV polynucleic acid of (a) with an oligonucleotide capable of discriminating a codon 181 encoding a serine from a codon 181 encoding an alanine or valine, and optionally also capable of discriminating one or more codons chosen from the group consisting of a codon 180 encoding a leucine from a codon 180 encoding a methionine, a codon 204 encoding an isoleucine from a codon 204 encoding a methionine, valine or serine, and a codon 236 encoding an asparagine from a codon 236 encoding a threonine
c) infering, from the discriminatory signal obtained in (b), the presence of said serine-encoding codon 181 of the HBV reverse transcriptase, optionally together with said methionine-encoding codon 180 or said isoleucine-encoding codon 204 or said asparagine-encoding codon 236 of the HBV reverse transcriptase domain and, therefrom, the resistance of an HBV virus present in said biological sample to an antiviral drug.

* * * * *